US007195651B2

(12) United States Patent
Plos et al.

(10) Patent No.: US 7,195,651 B2
(45) Date of Patent: Mar. 27, 2007

(54) COSMETIC COMPOSITION FOR DYEING HUMAN KERATIN MATERIALS, COMPRISING AT LEAST ONE FLUORESCENT DYE AND AT LEAST ONE CATIONIC POLYMER, AND A DYEING PROCESS THEREFOR

(75) Inventors: Grégory Plos, Paris (FR); Henri Samain, Bievres (FR)

(73) Assignee: L'Oreal S.A., Paris (FR)

( * ) Notice: Subject to any disclaimer, the term of this patent is extended or adjusted under 35 U.S.C. 154(b) by 327 days.

(21) Appl. No.: 10/814,335

(22) Filed: Apr. 1, 2004

(65) Prior Publication Data
US 2004/0258641 A1 Dec. 23, 2004

Related U.S. Application Data

(60) Provisional application No. 60/467,548, filed on May 5, 2003.

(30) Foreign Application Priority Data
Apr. 1, 2003 (FR) ................... 03 04026

(51) Int. Cl.
 *A61K 7/13* (2006.01)
(52) U.S. Cl. ................ 8/405; 8/406; 8/407; 8/410; 8/411; 8/421; 8/552; 8/554; 8/555; 8/648; 132/202; 132/208
(58) Field of Classification Search .......... 8/405, 8/406, 407, 410, 411, 421, 552, 554, 555, 8/648; 132/208, 202
See application file for complete search history.

(56) References Cited

U.S. PATENT DOCUMENTS

| 2,261,002 A | 10/1941 | Ritter |
| 2,271,378 A | 1/1942 | Searle |
| 2,273,780 A | 2/1942 | Ditmar |
| 2,375,853 A | 5/1945 | Kirby et al. |
| 2,388,614 A | 11/1945 | Kirby et al. |
| 2,454,547 A | 11/1948 | Bock et al. |
| 2,798,053 A | 7/1957 | Brown |
| 2,851,424 A | 9/1958 | Switzer et al. |
| 2,923,692 A | 2/1960 | Ackerman et al. |
| 2,961,347 A | 11/1960 | Floyd |
| 2,979,465 A | 4/1961 | Parran et al. |
| 3,014,041 A | 12/1961 | Hausermann et al. |
| 3,206,462 A | 9/1965 | McCarty |
| 3,227,615 A | 1/1966 | Korden |
| 3,472,840 A | 10/1969 | Stone et al. |
| 3,632,559 A | 1/1972 | Matter et al. |
| 3,639,127 A | 2/1972 | Brooker et al. |
| 3,658,985 A | 4/1972 | Olson, Jr. et al. |
| 3,856,550 A | 12/1974 | Bens et al. |
| 3,874,870 A | 4/1975 | Green et al. |
| 3,910,862 A | 10/1975 | Barabas et al. |
| 3,912,808 A | 10/1975 | Sokol |
| 3,915,921 A | 10/1975 | Schlatzer, Jr. |
| 3,917,817 A | 11/1975 | Vanlerberghe et al. |
| 3,929,990 A | 12/1975 | Green et al. |
| 3,966,904 A | 6/1976 | Green et al. |
| 3,986,825 A | 10/1976 | Sokol |
| 4,001,432 A | 1/1977 | Green et al. |
| 4,005,193 A | 1/1977 | Green et al. |
| 4,013,787 A | 3/1977 | Vanlerberghe et al. |
| 4,025,617 A | 5/1977 | Green et al. |
| 4,025,627 A | 5/1977 | Green et al. |
| 4,025,653 A | 5/1977 | Green et al. |
| 4,026,945 A | 5/1977 | Green et al. |
| 4,027,020 A | 5/1977 | Green et al. |
| 4,031,307 A | 6/1977 | DeMartino et al. |
| 4,075,136 A | 2/1978 | Schaper |
| 4,131,576 A | 12/1978 | Iovine et al. |
| 4,157,388 A | 6/1979 | Christiansen |
| 4,165,367 A | 8/1979 | Chakrabarti |
| 4,166,894 A | 9/1979 | Schaper |

(Continued)

FOREIGN PATENT DOCUMENTS

| AT | 302 534 | 10/1972 |
| CA | 1255603 | 6/1989 |
| CH | 487 231 | 3/1970 |
| DE | 33 13 332 | 10/1984 |
| DE | 196 46 804 A1 | 5/1997 |
| DE | 199 23 438 A1 | 11/2000 |

(Continued)

OTHER PUBLICATIONS

CAS Abstract for JP 2000-136340—Chemical Abstracts Service; Database Accession No. 2000: 317079; XP-002269220, JP 2000136340 (Pentel Co., Ltd), May 16, 2000.
Co-pending U.S. Appl. No. 10/742,995, filed Dec. 23, 2003.
Co-pending U.S. Appl. No. 10/814,334, filed Apr. 1, 2004.
Co-pending U.S. Appl. No. 10/814,333, filed Apr. 1, 2004.
Co-pending U.S. Appl. No. 10/814,430, filed Apr. 1, 2004.

(Continued)

*Primary Examiner*—Eisa Elhilo
(74) *Attorney, Agent, or Firm*—Finnegan, Henderson, Farabow, Garrett & Dunner L.L.P.

(57) ABSTRACT

The present disclosure relates to a cosmetic composition comprising at least one fluorescent dye comprising at least one fluorescent compound, and at least one cationic polymer with a charge density of at least 1 meq/g; processes that incorporate this cosmetic composition and to a kit comprising this cosmetic composition. The present disclosure also relates to the process for dyeing human keratin materials, including artificially dyed or pigmented hair and dark skin, with a lightening effect, comprising applying to the keratin materials a cosmetic composition comprising at least one fluorescent dye comprising at least one fluorescent compound and at least one cationic polymer with a charge density of at least 1 meq/g.

45 Claims, No Drawings

U.S. PATENT DOCUMENTS

| | | |
|---|---|---|
| 4,172,887 A | 10/1979 | Vanlerberghe et al. |
| 4,185,087 A | 1/1980 | Morlino |
| 4,189,468 A | 2/1980 | Vanlerberghe et al. |
| 4,197,865 A | 4/1980 | Jacquet et al. |
| 4,217,914 A | 8/1980 | Jacquet et al. |
| 4,223,009 A | 9/1980 | Chakrabarti |
| 4,237,243 A | 12/1980 | Quack et al. |
| 4,240,450 A | 12/1980 | Grollier et al. |
| 4,256,458 A | 3/1981 | Degen et al. |
| 4,277,581 A | 7/1981 | Vanlerberghe et al. |
| 4,381,919 A | 5/1983 | Jacquet et al. |
| 4,422,853 A | 12/1983 | Jacquet et al. |
| 4,445,521 A | 5/1984 | Grollier et al. |
| 4,509,949 A | 4/1985 | Huang et al. |
| 4,591,610 A | 5/1986 | Grollier |
| 4,608,250 A | 8/1986 | Jacquet et al. |
| 4,693,935 A | 9/1987 | Mazurek |
| 4,702,906 A | 10/1987 | Jacquet et al. |
| 4,719,099 A | 1/1988 | Grollier et al. |
| 4,719,282 A | 1/1988 | Nadolsky et al. |
| 4,728,571 A | 3/1988 | Clemens et al. |
| 4,761,273 A | 8/1988 | Grollier et al. |
| 4,781,724 A | 11/1988 | Wajaroff et al. |
| 4,823,985 A | 4/1989 | Grollier et al. |
| 4,839,166 A | 6/1989 | Grollier et al. |
| 4,948,579 A | 8/1990 | Jacquet et al. |
| 4,961,925 A | 10/1990 | Tsujino et al. |
| 4,972,037 A | 11/1990 | Garbe et al. |
| 4,996,059 A | 2/1991 | Grollier et al. |
| 5,009,880 A | 4/1991 | Grollier et al. |
| 5,057,311 A | 10/1991 | Kamegai et al. |
| 5,089,252 A | 2/1992 | Grollier et al. |
| 5,139,037 A | 8/1992 | Grollier et al. |
| 5,188,639 A | 2/1993 | Schultz et al. |
| 5,196,189 A | 3/1993 | Jacquet et al. |
| 5,275,808 A | 1/1994 | Murray et al. |
| 5,356,438 A | 10/1994 | Kim et al. |
| 5,445,655 A | 8/1995 | Kuhn et al. |
| 5,635,461 A | 6/1997 | Onitsuka et al. |
| 5,708,151 A | 1/1998 | Möckli |
| 5,733,343 A | 3/1998 | Mockli |
| 5,744,127 A * | 4/1998 | Giuseppe et al. ............. 424/59 |
| 5,792,221 A | 8/1998 | Lagrange et al. |
| 5,830,446 A | 11/1998 | Berthiaume et al. |
| 5,833,997 A | 11/1998 | Mahieu et al. |
| 5,853,708 A | 12/1998 | Cauwet et al. |
| 5,873,494 A | 2/1999 | Dallas, Jr. |
| 5,958,392 A | 9/1999 | Grollier et al. |
| 5,962,522 A | 10/1999 | Wacher et al. |
| 6,106,577 A | 8/2000 | Audousset et al. |
| 6,120,780 A | 9/2000 | Dupuis et al. |
| 6,180,666 B1 | 1/2001 | Wacher et al. |
| 6,260,556 B1 | 7/2001 | Legrand et al. |
| 6,375,958 B1 | 4/2002 | Cauwet et al. |
| 6,391,062 B1 | 5/2002 | Vandenbossche et al. |
| 6,436,151 B2 | 8/2002 | Cottard et al. |
| 6,436,153 B2 | 8/2002 | Rondeau |
| 6,475,248 B2 | 11/2002 | Ohashi et al. |
| 6,570,019 B2 | 5/2003 | Pasquier et al. |
| 6,576,024 B1 | 6/2003 | Lang et al. |
| 6,592,630 B2 | 7/2003 | Matsunaga et al. |
| 6,616,709 B2 | 9/2003 | Ohashi et al. |
| 6,712,861 B2 | 3/2004 | Rondeau |
| 2001/0010812 A1 | 8/2001 | Chevalier et al. |
| 2001/0023514 A1 | 9/2001 | Cottard et al. |
| 2001/0023515 A1 | 9/2001 | Cottard et al. |
| 2001/0031270 A1 | 10/2001 | Douin et al. |
| 2001/0034914 A1 | 11/2001 | Saunier et al. |
| 2001/0054206 A1* | 12/2001 | Matsunaga et al. ............. 8/405 |
| 2001/0055580 A1 | 12/2001 | Belli et al. |
| 2002/0004956 A1 | 1/2002 | Rondeau |
| 2002/0012681 A1 | 1/2002 | George et al. |
| 2002/0026676 A1 | 3/2002 | Ohashi et al. |
| 2002/0046431 A1* | 4/2002 | Laurent et al. ................. 8/405 |
| 2002/0046432 A1 | 4/2002 | Rondeau |
| 2002/0088063 A1 | 7/2002 | Ohashi et al. |
| 2002/0131941 A1 | 9/2002 | Habeck et al. |
| 2002/0176836 A9 | 11/2002 | Belli et al. |
| 2002/0176875 A9 | 11/2002 | Douin et al. |
| 2003/0000023 A9 | 1/2003 | Rondeau |
| 2003/0019052 A1 | 1/2003 | Pratt |
| 2003/0019053 A9 | 1/2003 | Rondeau |
| 2003/0055268 A1 | 3/2003 | Pasquier et al. |
| 2003/0074747 A1 | 4/2003 | Vuarier et al. |
| 2003/0124079 A1 | 7/2003 | Mougin et al. |
| 2003/0131424 A1 | 7/2003 | Audousset et al. |
| 2004/0019981 A1 | 2/2004 | Cottard et al. |
| 2004/0034945 A1 | 2/2004 | Javet et al. |
| 2004/0037796 A1 | 2/2004 | Cottard et al. |
| 2004/0049860 A1 | 3/2004 | Cottard et al. |
| 2004/0141943 A1 | 7/2004 | Mougin et al. |
| 2004/0148711 A1 | 8/2004 | Rondeau |
| 2004/0205901 A1 | 10/2004 | Cottard et al. |
| 2004/0258641 A1 | 12/2004 | Plos et al. |
| 2005/0005368 A1 | 1/2005 | Plos et al. |
| 2005/0005369 A1 | 1/2005 | Plos et al. |
| 2005/0008593 A1 | 1/2005 | Plos et al. |
| 2005/0028301 A1 | 2/2005 | Pastore |
| 2005/0144741 A1 | 7/2005 | Lang et al. |

FOREIGN PATENT DOCUMENTS

| | | |
|---|---|---|
| DE | 199 26 377 A1 | 12/2000 |
| DE | 100 29 441 A1 | 1/2002 |
| DE | 101 41 683 A1 | 6/2003 |
| DE | 101 48 844 A1 | 10/2003 |
| EP | 0 087 060 B1 | 8/1983 |
| EP | 0 095 238 A2 | 11/1983 |
| EP | 0 080 976 B1 | 9/1986 |
| EP | 0 173 109 | 10/1989 |
| EP | 0 370 470 B1 | 5/1990 |
| EP | 0 412 704 B1 | 2/1991 |
| EP | 0 412 707 B1 | 2/1991 |
| EP | 0 445 342 B1 | 9/1991 |
| EP | 0 486 135 B1 | 5/1992 |
| EP | 0 122 324 B2 | 2/1993 |
| EP | 0 337 354 B1 | 2/1994 |
| EP | 0 582 152 B1 | 2/1994 |
| EP | 0 395 282 | 3/1995 |
| EP | 0 503 853 | 5/1996 |
| EP | 0 714 954 A2 | 6/1996 |
| EP | 0 733 355 A2 | 9/1996 |
| EP | 0 815 828 B1 | 6/1999 |
| EP | 0 970 684 A1 | 1/2000 |
| EP | 1 023 891 B1 | 8/2000 |
| EP | 1 099 437 | 5/2001 |
| EP | 1 132 076 A1 | 9/2001 |
| EP | 1 133 977 A2 | 9/2001 |
| EP | 1 191 041 A2 | 3/2002 |
| FR | 1492597 | 9/1966 |
| FR | 1583363 | 10/1969 |
| FR | 2077143 | 10/1971 |
| FR | 2080759 | 11/1971 |
| FR | 2103210 | 7/1972 |
| FR | 2162025 | 7/1973 |
| FR | 2190406 | 2/1974 |
| FR | 2252840 | 6/1975 |
| FR | 2270846 | 12/1975 |
| FR | 2280361 | 2/1976 |
| FR | 2316271 | 1/1977 |
| FR | 2320330 | 3/1977 |
| FR | 2336434 | 7/1977 |
| FR | 2368508 | 5/1978 |
| FR | 2383660 | 10/1978 |

| | | |
|---|---|---|
| FR | 2393573 | 1/1979 |
| FR | 2411219 | 7/1979 |
| FR | 2416723 | 9/1979 |
| FR | 2470596 | 6/1981 |
| FR | 2505348 | 11/1982 |
| FR | 2519863 | 7/1983 |
| FR | 2542997 | 9/1984 |
| FR | 2586913 | 3/1987 |
| FR | 2589476 | 5/1987 |
| FR | 2598611 | 11/1987 |
| FR | 2692572 | 6/1992 |
| FR | 2741261 | 5/1997 |
| FR | 2 773 470 | 7/1999 |
| FR | 2 773 864 | 7/1999 |
| FR | 2 797 877 | 3/2001 |
| FR | 2800612 | 5/2001 |
| FR | 2811993 | 1/2002 |
| FR | 2820032 | 8/2002 |
| FR | 2830189 | 4/2003 |
| GB | 746864 | 3/1956 |
| GB | 759385 | 10/1956 |
| GB | 1214394 | 1/1970 |
| GB | 1546809 | 5/1979 |
| GB | 1554331 | 10/1979 |
| JP | 48-17362 | 5/1973 |
| JP | 54-86521 | 7/1979 |
| JP | 2-200612 | 8/1990 |
| JP | 6-128128 | 5/1994 |
| JP | 6-183935 | 7/1994 |
| JP | 6-227954 | 8/1994 |
| JP | 8-183716 | 7/1996 |
| JP | 8-208448 | 8/1996 |
| JP | 8-259426 | 10/1996 |
| JP | 9-183714 | 7/1997 |
| JP | 11-021214 | 1/1999 |
| JP | 10-236929 | 3/1999 |
| JP | 11-60453 | 3/1999 |
| JP | 11-343218 | 12/1999 |
| JP | 2000-01417 | 1/2000 |
| JP | 2000-86472 | 3/2000 |
| JP | 2000-505841 | 5/2000 |
| JP | 2001-172120 | 6/2001 |
| JP | 2001-220330 | 8/2001 |
| JP | 2001-226217 | 8/2001 |
| JP | 2001-261534 | 9/2001 |
| JP | 2001-261536 | 9/2001 |
| JP | 2001-294519 | 10/2001 |
| JP | 2001-302473 | 10/2001 |
| JP | 2001-516701 | 10/2001 |
| JP | 2001-516705 | 10/2001 |
| JP | 2001-516706 | 10/2001 |
| JP | 2001-516707 | 10/2001 |
| JP | 2002-12523 | 1/2002 |
| JP | 2002-12530 | 1/2002 |
| JP | 2002-047151 | 2/2002 |
| JP | 2002-226338 | 8/2002 |
| JP | 2002-249419 | 9/2002 |
| JP | 2002-326911 | 11/2002 |
| JP | 2003-55177 | 2/2003 |
| JP | 2004-059468 | 2/2004 |
| JP | 2004-307494 | 11/2004 |
| JP | 2004-307495 | 11/2004 |
| WO | WO 93/11103 | 6/1993 |
| WO | WO 93/23009 | 11/1993 |
| WO | WO 93/23446 | 11/1993 |
| WO | WO 94/02022 | 2/1994 |
| WO | WO 95/00578 | 1/1995 |
| WO | WO 95/01772 | 1/1995 |
| WO | WO 95/15144 | 6/1995 |
| WO | WO 99/13846 | 3/1996 |
| WO | WO 97/18795 | 5/1997 |
| WO | WO 99/12846 | 3/1999 |
| WO | WO 99/13822 | 3/1999 |
| WO | WO 99/13823 | 3/1999 |
| WO | WO 99/13824 | 3/1999 |
| WO | WO 99/13828 | 3/1999 |
| WO | WO 99/13841 | 3/1999 |
| WO | WO 99/13844 | 3/1999 |
| WO | WO 99/13845 | 3/1999 |
| WO | WO 99/13847 | 3/1999 |
| WO | WO 99/13849 | 3/1999 |
| WO | WO 99/20235 A1 | 4/1999 |
| WO | WO 00/68282 | 11/2000 |
| WO | WO 00/71085 A2 | 11/2000 |
| WO | WO 01/43714 A1 | 6/2001 |
| WO | WO 01/62759 A1 | 8/2001 |
| WO | WO 01/78669 | 10/2001 |
| WO | WO 02/32386 A2 | 4/2002 |
| WO | WO 02/38115 A1 | 5/2002 |
| WO | WO 02/39964 A1 | 5/2002 |
| WO | WO 02/45673 A2 | 6/2002 |
| WO | WO 02/58646 A1 | 8/2002 |
| WO | WO 02/58647 A1 | 8/2002 |
| WO | WO 02/74270 | 9/2002 |
| WO | WO 03/22232 A2 | 3/2003 |
| WO | WO 03/28685 A1 | 4/2003 |
| WO | WO 03/029359 | 4/2003 |

OTHER PUBLICATIONS

Co-pending U.S. Appl. No. 10/814,305, filed Apr. 1, 2004.
Co-pending U.S. Appl. No. 10/814,300, filed Apr. 1, 2004.
Co-pending U.S. Appl. No. 10/814,428, filed Apr. 1, 2004.
Co-pending U.S. Appl. No. 10/490,869, filed Apr. 1, 2004.
Co-pending U.S. Appl. No. 10/814,236, filed Apr. 1, 2004.
Co-pending U.S. Appl. No. 10/814,338, filed Apr. 1, 2004.
Co-pending U.S. Appl. No. 10/814,585, filed Apr. 1, 2004.
Co-pending U.S. Appl. No. 10/814,336, filed Apr. 1, 2004.
English language Derwent Abstract for DE 33 13 332.
English Language Derwent Abstract of DE 100 29 441.
English Language Derwent Abstract of DE 101 41 683.
English Language Derwent Abstract of DE 101 48 844.
English Language Derwent Abstract of DE 199 23 438.
English Language Derwent Abstract of DE 199 26 377.
English Language Derwent Abstract of EP 0 080 976.
English Language Derwent Abstract of EP 0 087 060.
English Language Derwent Abstract of EP 1 023 891.
English Language Derwent Abstract of EP 1 099 437.
English Language Abstract of FR 2 589 476 (EP 0 225 261) from EPO website.
English Language Derwent Abstract of FR 2 773,470.
English language abstract from esp@cenet for FR 2 797 877.
English Language Derwent Abstract of FR 2,800,612.
English Language Derwent Abstract of JP 2-200612.
English Language Derwent Abstract of JP 6-183935.
English Language Derwent Abstract of JP 6-227954.
English Language Derwent Abstract of JP 8-183716.
English Language Derwent Abstract of JP 8-208448.
English Language Derwent Abstract of JP 9-183714.
English Language Derwent Abstract of JP 10-236929.
English Language Derwent Abstract of JP 11-060453.
English Language Derwent Abstract of JP 11-21214.
English Language Derwent Abstract of JP 2000-1417.
English Language Derwent Abstract of JP 2000-086472.
English Language Derwent Abstract of JP 2001-172120.
English Language Derwent Abstract of JP 2001-22030.
English Language Derwent Abstract of JP 2001-261534.
English Language Abstract of JP 2001-294519 from Japio database.
English Language Derwent Abstract of JP 2001-302473.
English Language Derwent Abstract of JP 2001-516701.
English Language Derwent Abstract of JP 2001-516705.
English Language Derwent Abstract of JP 2001-516706.
English Language Derwent Abstract of JP 2001-516707.
English Language Abstract of JP 2002-047151 from Aurigin database.
English Language Derwent Abstract of JP 2002-226338.

English Language Abstract of JP 2002-249419 from Japio database.
English Language Derwent Abstract of JP 2002-326911.
English Language Derwent Abstract of JP 2004-59468.
English Language Derwent Abstract of WO 02/32386.
French Search Report for French Patent Application No. FR 02/16669, priority document for U.S. Appl. No. 10/742,995, Aug. 6, 2003.
French Search Report for French Patent Application No. FR 03/04021, priority document for U.S. Appl. No. 10/814,337, Dec. 8, 2003.
French Search Report for French Patent Application No. FR 03/04022, priority document for co-pending U.S. Appl. No. 10/814,336, Nov. 20, 2003.
French Search Report for French Patent Application No. FR 03/04024, priority document for co-pending application No. 10/814,585, Dec. 8, 2003.
French Search Report for French Patent Application No. FR 03/04026, priority document for co-pending U.S. Appl. No. 10/814,335, Nov. 21, 2003.
French Search Report for French Patent Application No. FR 03/04027, priority document for co-pending U.S. Appl. No. 10/814,428, Nov. 28, 2003.
French Search Report for French Patent Application No. FR 03/04028, priority document for co-pending U.S. Appl. No. 10/814,236, Nov. 25, 2003.
French Search Report for French Patent Application No. FR 03/04029, priority document for co-pending U.S. Appl. No. 10/814,430, Feb. 5, 2004.
French Search Report for French Patent Application No. FR 03/04030, priority document for co-pending U.S. Appl. No. 10/814,300, Nov. 27, 2003.
French Search Report for French Patent Application No. FR 03/04031, priority document for co-pending U.S. Appl. No. 10/814,333, Jan. 8, 2004.
French Search Report for French Patent Application No. FR 03/04033, priority document for co-pending U.S. Appl. No. 10/814,334, Nov. 28, 2003.
French Search Report for French Patent Application No. FR 03/04034, priority document for co-pending U.S. Appl. No. 10/814,338, Feb. 17, 2004.
French Search Report for French Patent Application No. FR 03/04035, priority document for co-pending U.S. Appl. No. 10/814,305, Feb. 5, 2004.
International Search Report for PCT Application No. PCT/FR 02/03252, (for co-pending U.S. Appl. No. 10/490,869), Jan. 20, 2003.
Office Action mailed Nov. 2, 2005 in co-pending U.S. Appl. No. 10/742,995.
Office Action mailed Apr. 6, 2006 in co-pending U.S. Appl. No. 10/742,995.
Office Action mailed Mar. 27, 2006 in co-pending U.S. Appl. No. 10/814,334.
Office Action mailed May 18, 2006 in co-pending U.S. Appl. No. 10/814,333.
Office Action mailed Jun. 8, 2006 in co-pending U.S. Appl. No. 10/814,430.
Office Action mailed Mar. 15, 2006 in co-pending U.S. Appl. No. 10/814,305.
Office Action mailed Aug. 24, 2006 in co-pending U.S. Appl. No. 10/814,305.
Office Action mailed Mar. 23, 2006 in co-pending U.S. Appl. No. 10/814,300.
Office Action mailed Aug. 28, 2006 in co-pending U.S. Appl. No. 10/814,300.
Office Action mailed Nov. 2, 2005 in co-pending U.S. Appl. No. 10/814,338.
Office Action mailed May 30, 2006 in co-pending U.S. Appl. No. 10/814,338.
Office Action mailed Nov. 3, 2005 in co-pending U.S. Appl. No. 10/490,869.
Office Action mailed May 26, 2006 in co-pending U.S. Appl. No. 10/490,869.
Office Action mailed Mar. 24, 2006 in co-pending U.S. Appl. No. 10/814,236.
Office Action mailed Aug. 28, 2006 in co-pending U.S. Appl. No. 10/814,236.
Office Action mailed Jul. 7, 2006 in co-pending U.S. Appl. No. 10/814,585.
Office Action mailed Nov. 17, 2005 in co-pending U.S. Appl. No. 10/814,336.
Office Action mailed Jun. 21, 2006 in co-pending U.S. Appl. No. 10/814,336.
Jacobi, Otto and Jacobi, Gertrud, "Investigation into the reciprocal action of cosmetics and the biosphere of the stratum corneuum of the skin," *Cosmetics and Toiletries*, 91:25-32 (Jan. 1976).
Science Des Traitements Capillaires [Hair Treatment Sciences] by Charles Zviak, 1988, published by Masson, pp. 215-278.
M. Schlossmann, "The Chemistry and Manufacture of Cosmetics Formulating," 2(3):522-526 (2000).
D.F. Williams et al., "Chemistry and Technology of the Cosmetics and Toiletries Industry," ed. 2, pp. 77-78 (1996).
Yuuki Kagoubutsu Jilen (Dictionary of Organic Compounds), Kodansha Ltd., Aug. 10, 2002, p. 908.
G. Fonnum, J. Bakke and Fk. Hansen—Colloid Polym. Sci 271, 380-389 (1993).
Zviak, C., The Science of Hair Care, pp. 215 and 278 (1986).

\* cited by examiner

COSMETIC COMPOSITION FOR DYEING HUMAN KERATIN MATERIALS, COMPRISING AT LEAST ONE FLUORESCENT DYE AND AT LEAST ONE CATIONIC POLYMER, AND A DYEING PROCESS THEREFOR

This application claims benefit of U.S. Provisional Application No. 60/467,548, filed May 5, 2003.

The present disclosure relates to cosmetic compositions comprising at least one fluorescent dye and at least one cationic polymer with a charge density of at least 1 meq/g, as well a dying processes involving the cosmetic composition as disclosed herein, and a device or kit comprising these cosmetic compositions. The present disclosure similarly relates to the use of a cosmetic composition comprising at least one fluorescent dye and at least one cationic polymer with a charge density of at least 1 meq/g, to dye with a lightening effect human keratin materials for example keratin fibers such as artificially dyed or pigmented hair, and also dark skin.

It is common for individuals who wish to lighten their skin and/or hair to use cosmetic or dermatological compositions containing bleaching agents. The substances most commonly used as bleaching agents are hydroquinone and its derivatives, kojic acid and its derivatives, azelaic acid, arbutin and its derivatives, alone or in combination with other active agents.

However, these agents are not without their drawbacks. For example, they may need to be used for a long time and in large amounts in order to obtain a bleaching effect on the skin. No immediate effect is observed when applying compositions comprising these common bleaching agents. Hydroquinone and its derivatives can be used in an amount that is effective to produce a visible bleaching effect. For example though, hydroquinone is known for its cytotoxicity towards melanocyte. Moreover, kojic acid and its derivatives can have the drawback of being expensive and consequently of not being able to practicably be used in large amounts in products for commercial mass distribution.

There is thus still a need for cosmetic compositions that allow a lighter, uniform, homogeneous skin tone of natural appearance to be obtained, wherein these cosmetic compositions have satisfactory transparency after application to the skin.

In the field of hair care, there are mainly two major types of hair dyeing.

One type is semi-permanent dyeing, also called direct dyeing, which uses dyes capable of giving the hair's original color a moderately pronounced modification that withstands multiple shampooing. These dyes are known as direct dyes and may be used in two different ways. The colorations may be performed by applying the composition containing at least one direct dye directly to the keratin fibers, or by applying a mixture, prepared extemporaneously, of a composition containing at least one direct dye with a composition containing an oxidizing bleaching agent, which can be, for example, an aqueous hydrogen peroxide solution. Such a process is then termed "lightening direct dyeing".

Another type is permanent dyeing or oxidation dyeing. This is performed with oxidation dye precursors, which are colorless or weakly colored compounds which, once mixed with oxidizing products, at the time of use, can give rise to colored compounds and dyes via a process of oxidative condensation. It is often desired to combine at least one direct dye with the oxidation bases and couplers in order to neutralize or attenuate the shades that may have too much of a red, orange or golden glint or, on the contrary, to accentuate these red, orange or golden glints.

Among the available direct dyes, nitrobenzene direct dyes may not be sufficiently strong, and indoamines, quinone dyes and natural dyes tend to have low affinity for keratin fibers and consequently lead to colorations that are not sufficiently fast with respect to the various treatments to which the fibers may be subjected, for example, with respect to shampooing.

In addition, there is often a desire to obtain a lightening effect on human keratin fibers. This lightening can be conventionally obtained via a process of bleaching the melanin of the hair via an oxidizing system which can comprise hydrogen peroxide optionally combined with persalts. This bleaching system can have the drawback of degrading the keratin fibers and of impairing their cosmetic properties.

The object of the present inventors was to solve the problems mentioned above and also to propose a cosmetic composition that may have at least one of good dyeing affinity for keratin materials such as keratin fibers, good resistance properties with respect to external agents, for example, with respect to shampooing, and that may make it possible to obtain lightening without damaging the treated material, such as the keratin fibers.

The inventors have thus found, surprisingly and unexpectedly, that the use of fluorescent dyes, for instance, those in the orange range, in the presence of particular cationic polymers, allows these objectives to be achieved.

One aspect of the present disclosure is thus a cosmetic composition comprising, in a cosmetically acceptable medium, at least one fluorescent dye that is soluble in the medium and at least one cationic polymer with a charge density of at least 1 meq/g; with the proviso that the at least one fluorescent dye is not 2-[2-(4-dialkylamino)phenylethenyl]-1-alkylpyridinium wherein the alkyl radical of the pyridinium nucleus is chosen from methyl and ethyl radicals, and the alkyl radical of the benzene nucleus is a methyl radical, and further wherein the counterion is a halide.

Another aspect of the present disclosure concerns a process for dyeing human keratin fibers with a lightening effect, comprising the performance of the following steps:

a) a cosmetic composition according to the present disclosure is applied to the fibers, for a time that is sufficient to develop the desired coloration and lightening, b) the fibers are optionally rinsed, c) the fibers are optionally washed with shampoo and rinsed, d) the fibers are dried or are left to dry.

Yet another aspect of the present disclosure concerns the method of use, for dyeing human keratin materials with a lightening effect, of a cosmetic composition comprising, in a cosmetically acceptable medium, at least one fluorescent dye that is soluble in the medium, and at least one cationic polymer with a charge density of at least 1 meq/g.

Still yet another aspect of the present disclosure is a multi-compartment device or kit for dyeing and lightening keratin fibers, comprising at least one compartment containing a cosmetic composition according to thepresent disclosure, and at least one other compartment containing a composition comprising at least one oxidizing agent.

The cosmetic compositions of the present disclosure may allow, for example, improved fixing of the fluorescent dye onto the keratin materials, which is reflected by an increased fluorescent effect, and a lightening effect that is greater than that obtained with the fluorescent dye used alone. Better resistance of the result with respect to washing or shampooing may also be found.

Unless otherwise indicated, the limits of the ranges of values that are given in the description are included in these ranges.

As has been discussed above, the cosmetic composition according to the present disclosure comprises at least one fluorescent dye and at least one cationic polymer with a charge density of at least 1 meq/g.

For the purposes of the present disclosure, the term "fluorescent dye" means a dye which comprises a molecule that colors by itself, and thus absorbs light in the visible spectrum and possibly in the ultraviolet spectrum (wavelengths ranging from about 360 to about 760 nanometres), but which, in contrast with a standard dye, converts the absorbed energy into fluorescent light of a longer wavelength than absorbed emitted in the visible region of the spectrum.

A fluorescent dye as disclosed herein is to be differentiated from an optical brightener. Optical brighteners, which are also known as brighteners, fluorescent brighteners, fluorescent brightening agents, fluorescent whitening agents, whiteners and fluorescent whiteners, are colorless transparent compounds, do not dye because they do not absorb light in the visible region, but only in the ultraviolet region (wavelengths ranging from about 200 to about 400 nanometres), and convert the absorbed energy into fluorescent light of a longer wavelength emitted in the visible region of the spectrum; the color impression is then generated solely by purely fluorescent light that is predominantly blue (wavelengths ranging from about 400 to about 500 nanometres).

Finally, the at least one fluorescent dye used in the cosmetic composition is soluble in the medium of the composition. It should be pointed out that the fluorescent dye differs therein from a fluorescent pigment, which itself is insoluble in the medium of the cosmetic composition.

For example, the at least one fluorescent dye used in the context of the present disclosure, which is optionally neutralized, is soluble in the medium of the cosmetic composition to at least 0.001 g/l at a temperature ranging from 15° C. to 25° C., for instance, at least 0.5 g/l, such as at least 1 g/l and, according to one aspect of the present disclosure, for example, at least 5 g/l at a temperature ranging from 15° C. to 25° C.

Moreover, according to one aspect of the present disclosure, the at least one fluorescent dye is not a 2-[2-(4-dialkylamino)phenylethenyl]-1-alkylpyridinium wherein the alkyl radical of the pyridinium nucleus is chosen from methyl and ethyl radicals and wherein the alkyl radical of the benzene nucleus is a methyl radical, and further wherein the counterion is a halide.

In accordance with another aspect of the present disclosure, the at least one fluorescent dye of the cosmetic composition is not a compound chosen from azo, azomethine and methine monocationic heterocyclic fluorescent dyes.

For example, the at least one fluorescent dye used according to the present disclosure can be chosen from dyes in the orange range. For instance, the fluorescent dyes of the present disclosure lead to a reflectance maximum that is in the wavelength range from about 500 to about 650 nanometres, such as in the wavelength range from about 550 to about 620 nanometres.

Some of the fluorescent dyes according to the present disclosure are compounds that are known per se. As examples of fluorescent dyes that may be used, non-limiting mention may be made of the fluorescent dyes belonging to the following families: naphthalimides; cationic and non-cationic coumarins; xanthenodiquinolizines (such as, for example, sulphorhodamines); azaxanthenes; naphtholactams; azlactones; oxazines; thiazines; dioxazines; polycationic fluorescent dyes of azo, azomethine and methine type, alone or as mixtures; and for instance, the following families: naphthalimides; cationic and non-cationic coumarins; azaxanthenes; naphtholactams; azlactones; oxazines; thiazines; dioxazines; polycationic fluorescent dyes of azo, azomethine and methine type, alone or as mixtures.

For further example, non-limiting mention may be made of the following dyes:

Brilliant Yellow B6GL sold by the company Sandoz and having the following structure:

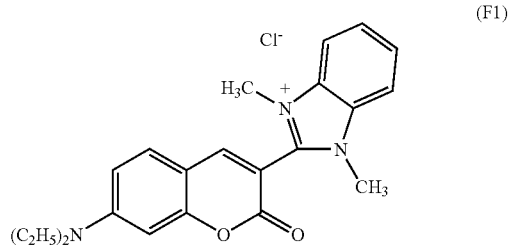

(F1)

Basic Yellow 2, or Auramine O, sold by the companies Prolabo, Aldrich or Carlo Erba and having the following structure:

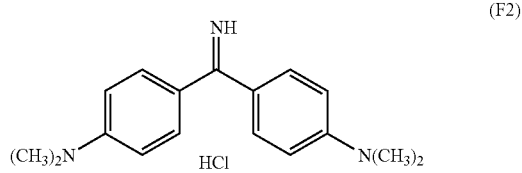

(F2)

also known as 4,4'-(imidocarbonyl)bis(N,N-dimethylaniline)monohydrochloride-CAS number 2465-27-2.

Non-limiting mention may further be made of the compounds having the following formula:

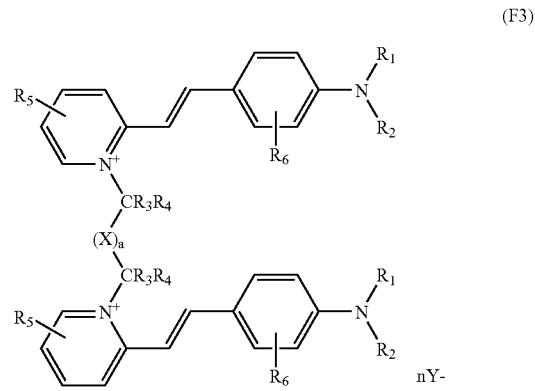

(F3)

wherein:

$R_1$ and $R_2$, which may be identical or different, are chosen from:
 hydrogen atoms;
 linear and branched alkyl radicals comprising from 1 to 10 carbon atoms, for example, from 1 to 4 carbon atoms, which may optionally be interrupted with at least one entity chosen from hetero atoms and groups comprising at least one hetero atom, and which may optionally be substituted with at least one entity chosen from hetero atoms, groups comprising at least one hetero atom, and halogen atoms;

aryl and arylalkyl radicals, wherein the aryl radicals comprise 6 carbon atoms and the alkyl radicals comprise from 1 to 4 carbon atoms; and further wherein the aryl radicals may optionally be substituted with at least one radical chosen from linear and branched alkyl radicals comprising from 1 to 4 carbon atoms, which may be optionally interrupted with at least one entity chosen from hetero atoms and groups comprising at least one hetero atom and optionally substituted with at least one entity chosen from hetero atoms, groups comprising at least one hetero atom, and halogen atoms;

$R_1$ and $R_2$ may optionally be linked so as to form a heterocycle with the nitrogen atom and may comprise at least one hetero atom, the heterocycle optionally being substituted with at least one linear or branched alkyl radical comprising for instance, from 1 to 4 carbon atoms and which may optionally be interrupted with at least one entity chosen from hetero atoms and groups comprising at least one hetero atom and/or optionally substituted with at least one entity chosen from hetero atoms, groups comprising at least one hetero atom, and halogen atoms;

$R_1$ or $R_2$ may optionally be included in a heterocycle comprising the nitrogen atom and one of the carbon atoms of the phenyl group comprising the nitrogen atom;

$R_3$ and $R_4$, which may be identical or different, may be chosen from hydrogen atoms and alkyl radicals containing from 1 to 4 carbon atoms;

$R_5$, which may be identical or different, may be chosen from hydrogen atoms, halogen atoms, and linear and branched alkyl radicals comprising from 1 to 4 carbon atoms, which may be optionally interrupted with at least one hetero atom;

$R_6$, which may be identical or different, may be chosen from hydrogen atoms; halogen atoms; and linear and branched alkyl radicals comprising from 1 to 4 carbon atoms, which may optionally be interrupted with a least one entity chosen from hetero atoms and groups comprising at least one hetero atom, and which may optionally be substituted with at least one entity chosen from hetero atoms, groups comprising at least one hetero atom, and halogen atoms;

X may be chosen from:
linear and branched alkyl radicals comprising from 1 to 14 carbon atoms and alkenyl radicals comprising from 2 to 14 carbon atoms, wherein the radicals may be optionally interrupted with at least one entity chosen from hetero atoms and groups comprising at least one hetero atom, and optionally substituted with at least one entity chosen from hetero atoms, groups containing at least one hetero atom, and halogen atoms;

5- and 6-membered heterocyclic radicals optionally substituted with at least one entity chosen from linear and branched alkyl radicals comprising from 1 to 14 carbon atoms, optionally substituted with at least one hetero atom; linear and branched aminoalkyl radicals comprising from 1 to 4 carbon atoms, optionally substituted with at least one hetero atom; and halogen atoms;

fused and non-fused aromatic and diaromatic radicals, optionally separated with at least one alkyl radical containing from 1 to 4 carbon atoms, wherein the aromatic and diaromatic radicals may optionally be substituted with at least one entity chosen from halogen atoms, alkyl radicals comprising from 1 to 10 carbon atoms optionally interrupted with at least one entity chosen from hetero atoms and groups comprising at least one hetero atom, and optionally substituted with at least one entity chosen from hetero atoms and groups comprising at least one hetero atom;

dicarbonyl radicals;

the group X optionally comprises at least one cationic charge;

a is equal to 0 or 1;

$Y^-$, which may be identical or different, is chosen from organic and mineral anions; and n is an integer ranging from 2 to the number of cationic charges present in the fluorescent compound.

It should be recalled that the term "hetero atom" represents an oxygen or nitrogen atom. Among the groups comprising hetero atoms, non-limiting mention may be made of hydroxyl, alkoxy, carbonyl, amino, ammonium, amido (—N—CO—) and carboxyl (—O—CO— or —CO—O—) groups.

With respect to the alkenyl groups, they may comprise at least one unsaturated carbon-carbon bond (—C═C—) and for example, one carbon-carbon double bond.

In this general formula, the radicals $R_1$ and $R_2$, which may be identical or different, may be chosen from, for example:
hydrogen atoms;
alkyl radicals comprising from 1 to 10 carbon atoms, for instance from 1 to 6 carbon atoms, such as from 1 to 4 carbon atoms, which may optionally be interrupted with an oxygen atom, or optionally substituted with at least one entity chosen from hydroxyl, amino and ammonium radicals, and chlorine and fluorine atoms;

benzyl and phenyl radicals optionally substituted with alkyl and alkoxy radicals containing from 1 to 4 carbon atoms, for instance from 1 or 2 carbon atoms; and forming with the nitrogen atom, a heterocyclic radical chosen from pyrrolo, pyrrolidino, imidazolino, imidazolo, imidazolium, pyrazolino, piperazino, morpholino, morpholo, pyrazolo, and triazolo radicals, optionally substituted with at least one linear or branched alkyl radical comprising from 1 to 4 carbon atoms optionally interrupted with at least one entity chosen from nitrogen, oxygen, and groups comprising at least one nitrogen or oxygen, and optionally substituted with at least one entity chosen from nitrogen atoms, oxygen atoms, and groups comprising a nitrogen and/or oxygen atom.

With respect to the abovementioned amino and ammonium radicals, the radicals borne by the nitrogen atom may be identical or different and may, for example, be chosen from hydrogen atoms, $C_1$–$C_{10}$ alkyl radicals, such as $C_1$–$C_4$ alkyl radicals, arylalkyl radicals wherein, for instance, the aryl radical contains 6 carbon atoms and the alkyl radical contains from 1 to 10 carbon atoms, for example, from 1 to 4 carbon atoms.

According to one aspect of the present disclosure, the radicals $R_1$ and $R_2$, which may be identical or different, may be chosen from hydrogen atoms; linear and branched $C_1$–$C_6$ alkyl radicals; $C_2$–$C_6$ alkyl radicals substituted with a hydroxyl radical; $C_2$–$C_6$ alkyl radicals comprising a group chosen from amino and ammonium groups; $C_2$–$C_6$ chloroalkyl radicals; $C_2$–$C_6$ alkyl radicals interrupted with an oxygen atom or substituted with a group comprising an oxygen atom, for example ester; aromatic radicals, for instance phenyl, benzyl and 4-methylphenyl; heterocyclic radicals such as pyrrolo, pyrrolidino, imidazolo, imidazolino, imidazolium, piperazino, morpholo, morpholino, pyrazolo and triazolo radicals, optionally substituted with at least one radical chosen from $C_1$–$C_6$ alkyls and aromatic radicals.

For example, the radicals $R_1$ and $R_2$, which may be identical or different, may be chosen from hydrogen atoms, linear and branched $C_1$–$C_6$ alkyl radicals, such as methyl, ethyl, n-butyl and n-propyl radicals; 2-hydroxyethyl radicals; alkyltrimethylammonium and alkyltriethylammonium radicals, wherein the alkyl radical comprises linear $C_2$–$C_6$ alkyl radical; (di)alkylmethylamino and (di)alkylethylamino radicals, wherein the alkyl radical comprises linear $C_1$–$C_6$ alkyl radicals; —$CH_2CH_2Cl$; —$(CH_2)_n$—$OCH_3$ and —$(CH_2)_n$—$OCH_2CH_3$ wherein n is an integer ranging from 2 to 6; —$CH_2CH_2$—$OCOCH_3$; and —$CH_2CH_2COOCH_3$.

For further example, the radicals $R_1$ and $R_2$, which may be identical or different, may be identical, and chosen from methyl radicals and ethyl radicals.

The radicals $R_1$ and $R_2$, which may be identical or different, may also be heterocyclic radicals chosen from pyrrolidino, 3-aminopyrrolidino, 3-(dimethyl)-aminopyrrolidino, 3-(trimethyl)aminopyrrolidino, 2,5-dimethylpyrrolo, 1H-imidazolo, 4-methylpiperazino, 4-benzylpiperazino, morpholo, 3,5-(tert-butyl)-1H-pyrazolo, 1H-pyrazolo and 1H-1,2,4-triazolo type.

The radicals $R_1$ and $R_2$, which may be identical or different, may also be linked so as to form a heterocycle of formulae (I) and (II):

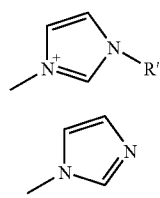

(I)

(II)

wherein R' is chosen from hydrogen atoms and $C_1$–$C_3$ alkyl radicals, —$CH_2CH_2OH$, and —$CH_2CH_2OCH_3$.

In accordance with one aspect of the present disclosure, $R_5$, which may be identical or different, may be chosen from hydrogen, fluorine, and chlorine atoms, and linear and branched alkyl radicals comprising from 1 to 4 carbon atoms optionally interrupted with an oxygen or nitrogen atom.

It is noted that the substituent $R_5$, if it is other than hydrogen, may be, for example, in position 3 and/or position 5 relative to the carbon of the ring comprising the nitrogen substituted with the radicals $R_1$ and $R_2$, for instance in position 3 relative to that carbon.

For further example, the radicals $R_5$, which may be identical or different, may be chosen from hydrogen atoms; linear and branched $C_1$–$C_4$ alkyl radicals; —$O$—$R_{51}$ wherein $R_{51}$ comprises linear $C_1$–$C_4$ alkyl radicals; —$R_{52}$—$O$—$CH_3$, wherein $R_{52}$ comprises linear $C_2$–$C_3$ alkyl radicals; —$R_{53}$—$N(R_{54})_2$, wherein $R_{53}$ comprises linear $C_2$–$C_3$ alkyl radicals and $R_{54}$, which may be identical or different, may be chosen from hydrogen atoms and methyl radicals.

As yet another example, $R_5$, which may be identical or different, may be chosen from hydrogen atoms, and methyl and methoxy radicals; for instance, $R_5$ may comprise a hydrogen atom.

According to one aspect of the present disclosure, $R_6$, which may be identical or different, may be chosen from hydrogen atoms; linear and branched $C_1$–$C_4$ alkyl radicals;

—X wherein X may be chosen from chlorine, bromine and fluorine atoms; —$R_{61}$—$O$—$R_{62}$ wherein $R_{61}$ comprises linear $C_2$–$C_3$ alkyl radicals and $R_{62}$ comprises a methyl radical; —$R_{63}$—$N(R_{64})_2$, wherein $R_{63}$ comprises linear $C_2$–$C_3$ alkyl radicals and $R_{64}$, which may be identical or different, may be chosen form hydrogen atoms and methyl radicals; —$N(R_{65})_2$, wherein $R_{65}$, which may be identical or different, may be chosen from hydrogen atoms and linear $C_2$–$C_3$ alkyl radicals; —$NHCOR_{66}$ wherein $R_{66}$ may be chosen from $C_1$–$C_2$ alkyl radicals, $C_1$–$C_2$ chloroalkyl radicals; and —$R_{67}$—$NH_2$, —$R_{67}$—$NH(CH_3)$, —$R_{67}$—$N(CH_3)_2$, —$R_{67}$—$N^+(CH_3)_3$, and —$R_{67}$—$N^+(CH_2CH_3)_3$ radicals wherein $R_{67}$ comprises $C_1$–$C_2$ alkyl radicals.

It is noted that the substituent $R_6$, if it is other than hydrogen, may be, for example in position 2 and/or position 4 relative to the nitrogen atom of the pyridinium ring, for instance in position 4 relative to that nitrogen atom. For further example, t$R_6$, which may be identical or different, may be chosen from hydrogen atoms and methyl and ethyl radicals, for instance, $R_6$ may comprise a hydrogen atom.

With respect to $R_3$ and $R_4$, these radicals, which may be identical or different, may, for example, be chosen from hydrogen atoms and alkyl radicals containing from 1 to 4 carbon atoms, such asd methyl radicals. For further example, $R_3$ and $R_4$ may each comprise hydrogen atoms.

As disclosed herein, X may be chosen from:
linear and branched alkyl radicals comprising from 1 to 14 carbon atoms and alkenyl radicals comprising from 2 to 14 carbon atoms, which may be optionally interrupted with at least one hetero atom and optionally substituted with at least one entity chosen from hetero atoms, groups comprising at least one hetero atom, and halogen atoms;

5- 6-membered heterocyclic radicals which may be optionally substituted with at least one entity chosen from linear and branched alkyl radicals containing from 1 to 14 carbon atoms; linear and branched aminoalkyl radicals containing from 1 to 4 carbon atoms, optionally substituted with at least one hetero atom; and halogen atoms;

fused and non-fused aromatic and diaromatic radicals, optionally interrupted with an alkyl radical comprising from 1 to 4 carbon atoms, wherein the aryl radical may optionally be substituted with at least one entity chosen from halogen atoms and alkyl radicals comprising from 1 to 10 carbon atoms, wherein the alkyl radicals may optionally be interrupted with at least one hetero atom and optionally substituted with at least one entity chosen from hetero atoms, and groups comprising at least one hetero atom;

dicarbonyl radicals.

In addition, it is possible for the group X to comprise at least one cationic charge.

Thus, X may be chosen from linear and branched alkyl radicals comprising from 1 to 14 carbon atoms, and alkenyl radicals comprising from 2 to 14 carbon atoms, and wherein X may optionally be interrupted with at least one hetero atom chosen from oxygen and nitrogen atoms, and may optionally be substituted with at least one entity chosen from hetero atoms chosen from oxygen and nitrogen atoms, groups comprising at least one hetero atom, and halogens chosen from fluorine and chlorine atoms. Among the groups of this type, non-limiting mention may be made, for example, of hydroxyl, alkoxy, for instance, with a radical R of the $C_1$–$C_4$ alkyl type, amino, ammonium, amido, carbonyl and carboxyl groups, i.e., —COO— and —O—CO—, such as with a radical of alkyloxy type.

It should be noted that the nitrogen atom, if it is present, may be in a quaternized or non-quaternized form. When a nitrogen atom is present, the at least one other radical borne by the quaternized or non-quaternized nitrogen atom may be identical or different, and may be chosen from hydrogen atoms and $C_1$–$C_4$ alkyl radicals, such as methyl.

According to another aspect of the present disclosure, the group X may comprise 5- and/or 6-membered heterocyclic radicals chosen from imidazolo, pyrazolo, triazino and pyridino radicals, which may be optionally substituted with at least one entity chosen from linear and branched alkyl radicals coomprising from 1 to 14 carbon atoms, for instance from 1 to 10 carbon atoms, such as from 1 to 4 carbon atoms; and linear and branched aminoalkyl radicals comprising from 1 to 10 carbon atoms, for example, from 1 to 4 carbon atoms, optionally substituted with an entity chosen from groups comprising at least one hetero atom, such as hydroxyl radicals, and halogen atoms. It should be noted that the amino group may be linked to the heterocycle.

In accordance with another aspect of the present disclosure, X may be chosen from aromatic radicals, for example comprising 6 carbon atoms, and fused and non-fused diaromatic radicals, for instance comprising from 10 to 12 carbon atoms, optionally separated with an alkyl radical containing from 1 to 4 carbon atoms, wherein the aryl radicals may optionally be substituted with at least one entity chosen from halogen atoms and alkyl radicals containing from 1 to 10 carbon atoms, such as from 1 to 4 carbon atoms, wherein the alkyl radicals may optionally be interrupted with at least one entity chosen from oxygen atoms, nitrogen atoms, and groups comprising at least one hetero atom, for instance carbonyl, carboxyl, amido, amino and ammonium radicals.

The aromatic radical, for example, a phenyl radical, may be linked to the groups $CR_3R_4$ via bonds in positions 1,2; 1,3 or 1,4, such as in positions 1,3 and 1,4. If the phenyl radical linked via bonds in positions 1,4 bears one or two substituents, the at least one substituent may be located in position 1 and/or 4 relative to one of the groups $CR_3R_4$. If the phenyl radical linked via bonds in positions 1,3 bears one or two substituents, the at least one substituent may be located in position 1 and/or 3 relative to one of the groups $CR_3R_4$.

In the case where X is diaromatic, it may be, for example, non-fused and comprise two phenyl radicals optionally separated with an entity chosen from single bonds, i.e., a carbon of each of the two rings, and alkyl radicals, such as $CH_2$ and $C(CH_3)_2$. For example, the aromatic radicals do not have to bear a substituent. It should be noted that the diaromatic radical is linked to the groups $CR_3R_4$ via bonds in positions 4,4'.

As examples of groups that X may be chosen from, non-limiting mention may be made of, for example, linear and branched alkyl radicals comprising from 1 to 13 carbon atoms, such as methylene, ethylene, propylene, isopropylene, n-butylene, pentylene and hexylene; 2-hydroxypropylene and 2-hydroxy-n-butylene; $C_1$–$C_{13}$ alkylene radicals interrupted with at least one hetero atom chosen from nitrogen and oxygen atoms, and/or substituted with at least entity chosen from nitrogen atoms, oxygen atoms, and groups comprising at least one hetero atom, for instance hydroxyl, amino, ammonium, carbonyl and carboxyl groups, for example, such as —$CH_2CH_2OCH_2CH_2$—, 1,6-dideoxy-d-mannitol, —$CH_2N^+(CH_3)_2CH_2$—, —$CH_2CH_2N^+(CH_3)_2$—$(CH_2)_6N^+(CH_3)_2$—$CH_2CH_2$—, CO—CO—, 3,3-di-methylpentylene, 2-acetoxyethylene, butylene-1,2,3,4-tetraol; —CH=CH—; aromatic and diaromatic radicals substituted with at least one entity chosen from halogen atoms, and alkyl radicals, with at least one group comprising at least one hetero atom, such as 1,4-phenylene, 1,3-phenylene, 1,2-phenylene, 2,6-fluorobenzene, 4,4'-biphenylene, 1,3-(5-methylbenzene), 1,2-bis(2-methoxy)benzene, bis(4-phenyl)methane, methyl 3,4-benzoate and 1,4-bis(amidomethyl)phenyl; heterocyclic radicals such as pyridine, and derivatives thereof such as 2,6-bispyridine, imidazole, imidazolium and triazine.

According to still another aspect of the present disclosure, X may be chosen from linear and branched $C_1$–$C_{13}$ alkyl radicals; —$CH_2CH(OH)CH_2$—; —$CH_2CH(Cl)CH_2$—; —$CH_2CH_2$—$OCOCH_2$—; —$CH_2CH_2COOCH_2$—; —Ra—O—Rb— wherein Ra comprises linear $C_2$–$C_6$ alkyl radicals and Rb comprises linear $C_1$–$C_2$ alkyl radicals; —Rc—N(Rd)—Re— wherein Rc comprises $C_2$–$C_9$ alkyl radicals, Rd is chosen from hydrogen atoms and $C_1$–$C_2$ alkyl radicals and Re comprises $C_1$–$C_6$ alkyl radicals; —RfN$^+$(Rg)$_2$—Rh— wherein Rf comprises linear $C_2$–$C_9$ alkyl radicals, Rg, which may be, for example, identical, comprises $C_1$–$C_2$ alkyl radicals and Rh comprises linear $C_1$–$C_6$ alkyl radicals; and —CO—CO—.

X may further comprise an imidazole radical, optionally substituted with at least one alkyl radical containing from 1 to 14 carbon atoms, such as from 1 to 10 carbon atoms, and for instance, from 1 to 4 carbon atoms, for example the divalent radicals of formula (III)

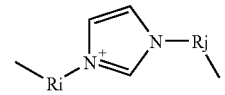

wherein Ri and Rj, which may be identical or different, comprise linear $C_1$–$C_6$ alkyl radicals;

X may also be chosen from the divalent triazine-based radicals of the following formulae

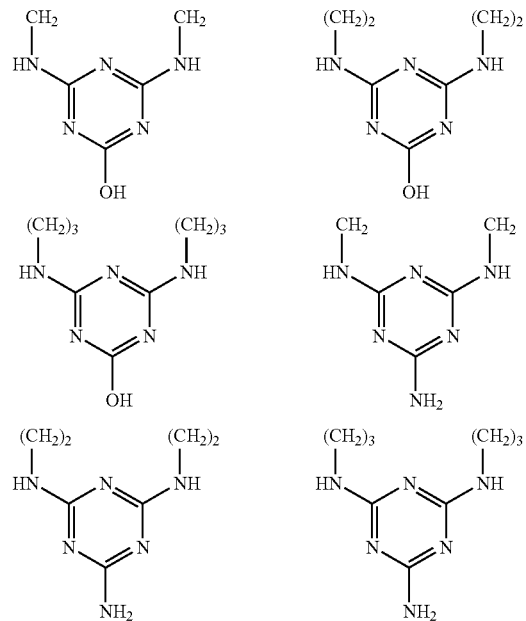

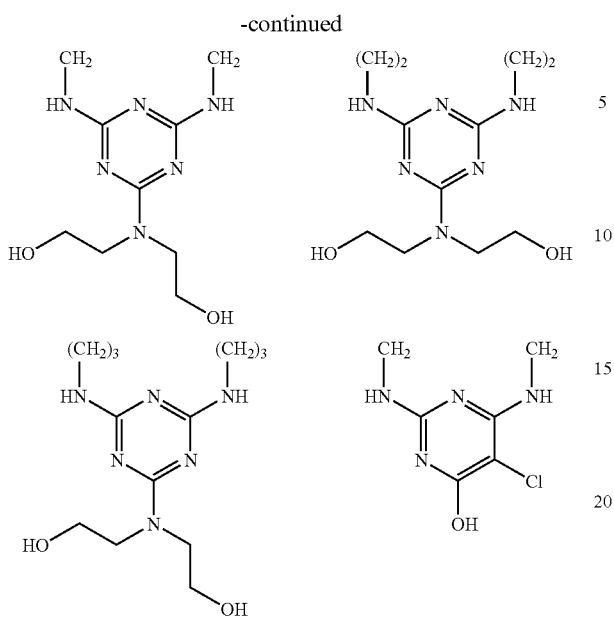

According to another aspect of the present disclosure, X may be chosen from the divalent aromatic radicals below:

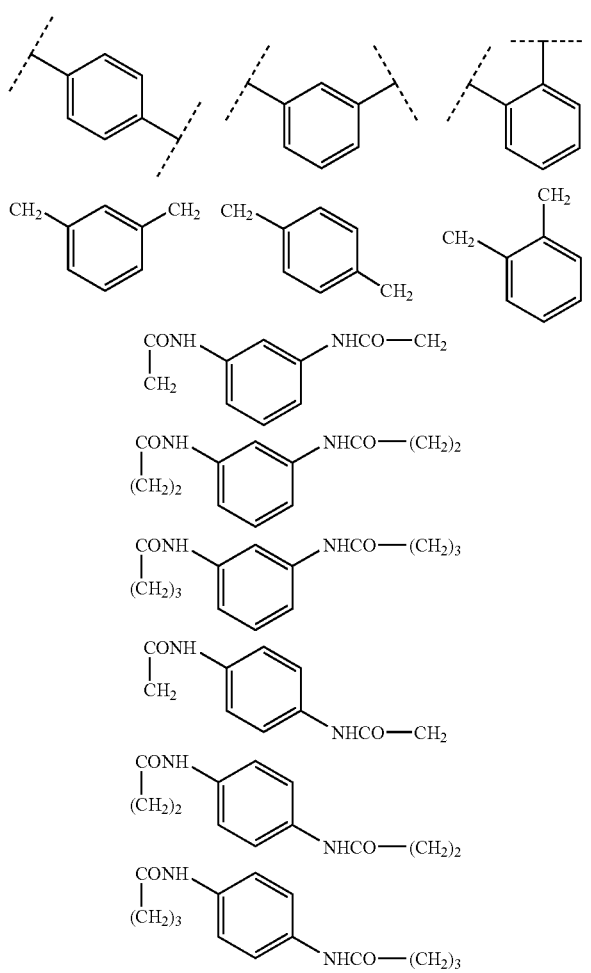

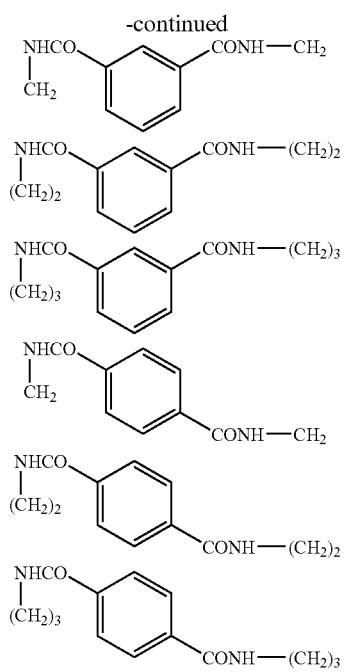

In the general formula of the fluorescent compounds described herein, $Y^-$ represents an organic or mineral anion. If there are several anions $Y^-$, these anions may be identical or different.

Among the anions of mineral origin that may be mentioned, without wishing to be limited thereto, are anions derived from halogen atoms, such as chlorides, iodides, sulphates bisulphates, nitrates, phosphates, hydrogen phosphates, dihydrogen phosphates, carbonates and bicarbonates.

Among the anions of organic origin that may be mentioned, without wishing to be limited thereto, are anions derived from the salts of saturated or unsaturated, aromatic or non-aromatic monocarboxylic or polycarboxylic, sulphonic or sulphuric acids, optionally substituted with at least one entity chosen from halogen atoms, and hydroxyl and amino radicals. Non-limiting examples of organic anions include acetates, hydroxyacetates, aminoacetates, (tri)chloroacetates, benzoxyacetates, propionates and derivatives comprising a chlorine atom, fumarates, oxalates, acrylates, malonates, succinates, lactates, tartrates, glycolates, citrates, benzoates and derivatives comprising a methyl or amino radical, alkyl sulphates, tosylates, benzenesulphonates, toluenesulphonates, etc.

For example, the anions Y, which may be identical or different, may be chosen from chloride, sulphate, methosulphate and ethosulphate.

As discussed above, the integer n ranges from 2 to the number of cationic charges present in the fluorescent compound.

For example, the fluorescent compounds according to the present disclosure may be symmetrical compounds. These fluorescent compounds may be synthesized by reacting, in a first step, α-picoline with a reagent comprising two leaving groups that may be chosen from halogen atoms, such as bromine and chlorine, tolylsulphonyl and methane-sulphonyl radicals. This first step may optionally take place in the presence of a solvent, for instance dimethylformamide. The number of moles of α-picoline is generally about 2 per mole of reagent comprising the leaving groups.

In addition, the reaction is usually performed at the reflux temperature of the reagent and/or of the solvent if a solvent is present. The product derived from this first step is then placed in contact with a corresponding aldehyde having the following formula:

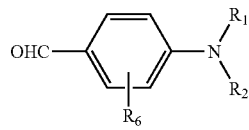

wherein $R_1$, $R_2$ and $R_6$ have the same meanings as disclosed herein above.

the reaction may be performed in the presence of a suitable solvent, which may be, for example, at reflux.

It is also possible to use an aldehyde for which $R_1$, $R_2$ and $R_6$ comprise hydrogen atoms, and to perform, in accordance with standard methods, the substitution of these hydrogen atoms with suitable radicals as described in the general formula, once the second step is complete. Reference may be made to, for instance, syntheses as described in U.S. Pat. No. 4,256,458.

The at least one fluorescent dye as disclosed herein may be present in the cosmetic composition in an amount ranging from 0.01% to 20% by weight, for instance from 0.05% to 10% by weight, and such as from 0.1% to 5% by weight, relative to the total weight of the cosmetic composition.

The cosmetic composition further comprises at least one cationic polymer with a charge density of at least 1 meq/g. This charge density is determined via the Kjeldahl method.

For the purposes of the present disclosure, the expression "cationic polymer" means any polymer containing cationic groups and/or groups that can be ionized into cationic groups. For example, the cationic polymers that may be used in accordance with the present disclosure may be chosen from those described for instance, in EP 337,354, FR 2,270, 846, FR 2,383,660, FR 2,598,611, FR 2,470,596 and FR 2,519,863.

Among the cationic polymers that may be used, non-limiting mention may be made of those containing units comprising primary, secondary, tertiary and/or quaternary amine groups, which may either form part of the main polymer chain or may be borne by a side substituent directly attached thereto.

The cationic polymers that may be used generally have a number-average molecular mass ranging from about 500 to about $5\times10^6$ such as from about $10^3$ to about $3\times10^6$.

Further among the cationic polymers that may be used, non-limiting mention may be made of polyamine, polyamino amide and polyquaternary ammonium polymers. These are known polymers and are described for instance in patents FR 2,505,348 and FR 2,542,997. Further still among the polymers, non-limiting mention may be made of:

(1) Homopolymers and copolymers derived from acrylic and/or methacrylic esters and/or amides and comprising at least one of the units of formula (I), (II), (III) or (IV) below:

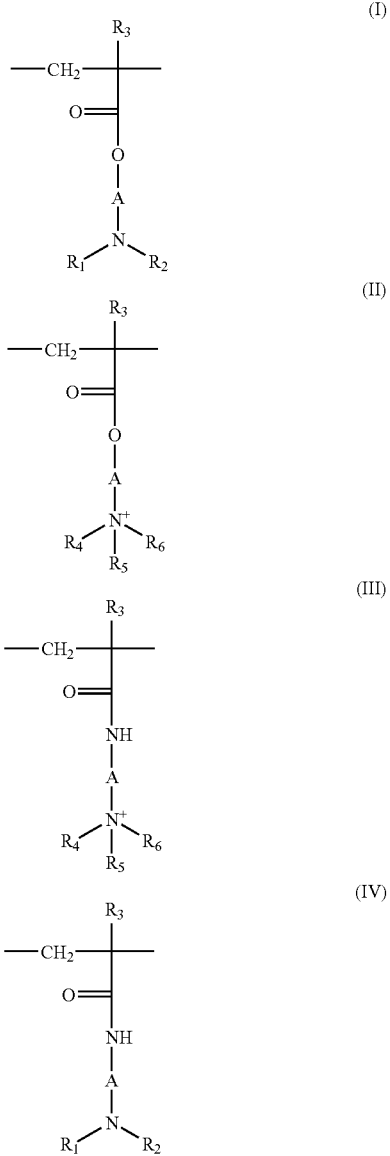

wherein:

$R_3$, which may be identical or different, may be chosen from hydrogen atoms and $CH_3$ radicals;

A, which may be identical or different, may be chosen from linear and branched $C_1$–$C_6$, such as $C_2$–$C_3$, alkyl groups and $C_1$–$C_4$ hydroxyalkyl groups;

$R_4$, $R_5$ and $R_6$, which may be identical or different, may be chosen from $C_1$–$C_{18}$ alkyl groups and benzyl radicals, and preferably a $C_1$–$C_6$ alkyl group;

$R_1$ and $R_2$, which may be identical or different, are chosen from hydrogen atoms and $C_1$–$C_6$ alkyl groups, such as methyl and ethyl;

X may be chosen from anions derived from inorganic and organic acid, such as methosulphate anions, andhalides, such as chloride and bromide.

The polymers of family (1) can also contain at least one unit derived from comonomers which may be chosen from the family of acrylamides, methacrylamides, diacetone acrylamides, acrylamides and methacrylamides substituted on the nitrogen with lower, i.e., $C_1$–$C_4$, alkyls, acrylic and methacrylic acids and esters thereof, vinyllactams, such as vinylpyrrolidone and vinylcaprolactam, and vinyl esters.

Thus, among the polymers of family (1), non-limiting mention may be made of:

copolymers of acrylamide and of dimethylaminoethyl methacrylate quaternized with dimethyl sulphate or with a dimethyl halide, such as the product sold under the name Hercofloc by the company Hercules, the copolymers of acrylamide and of methacryloyloxyethyltrimethylammonium chloride described, for example, in EP 80,976 and sold under the name Bina Quat P 100 by the company Ciba Geigy, the copolymers of acrylamide and of methacryloyloxyethyltrimethylammonium methosulphate sold under the name Reten by the company Hercules, quaternized or non-quaternized vinylpyrrolidone/dialkylaminoalkyl acrylate or methacrylate copolymers, such as the products sold under the name "Gafquat" by the company ISP, such as, for example, "Gafquat 734" or "Gafquat 755," or alternatively the products known as "Copolymer 845, 958 and 937;" these polymers are described in FR 2,077,143 and FR 2,393,573, dimethylaminoethyl methacrylate/vinylcaprolactam/vinylpyrrolidone terpolymers, such as the product sold under the name Gaffix VC 713 by the company ISP, vinylpyrrolidone/methacrylamidopropyldimethylamine copolymers, for example, those sold under the name Styleze CC 10 by ISP, and quaternized vinylpyrrolidone/dimethylaminopropyl methacrylamide copolymers such as the product sold under the name "Gafquat HS 100" by the company ISP.

(2) The cellulose ether derivatives containing quaternary ammonium groups, described in French Patent No. 1,492,597, and for instance, polymers sold under the name "JR," such as JR 400, JR 125 and JR 30M, or "LR," such as LR 400 or LR 30M, by the company Union Carbide Corporation. These polymers are also defined in the CTFA dictionary as quaternary ammoniums of hydroxyethylcellulose that have reacted with an epoxide substituted with a trimethylammonium group.

(3) Cationic cellulose derivatives such as cellulose copolymers or cellulose derivatives grafted with a water-soluble quaternary ammonium monomer, for example, those described in U.S. Pat. No. 4,131,576, such as hydroxyalkylcelluloses, for instance hydroxymethyl-, hydroxyethyl- or hydroxypropylcelluloses grafted, for instance, with a methacryloylethyltrimethylammonium, methacrylamidopropyltrimethylammonium or dimethyldiallylammonium salt. For example, some commercial products corresponding to this definition are the products sold under the names "Celquat L 200" and "Celquat H 100" by the company National Starch.

(4) The cationic polysaccharides described for example in U.S. Pat. Nos. 3,589,578 and 4,031,307, such as guar gums containing cationic trialkylammonium groups. Guar gums modified with a salt, e.g. chloride, of 2,3-epoxypropyltrimethylammonium are used, for example. Such products are sold in particular under the trade names Jaguar C13S, Jaguar C15, Jaguar C17 and Jaguar C162 by the company Meyhall.

(5) Polymers comprising piperazinyl units and divalent alkylene or hydroxyalkylene radicals containing straight or branched chains, optionally interrupted by oxygen, sulphur or nitrogen atoms or by aromatic or heterocyclic rings, as well as the oxidation and/or quaternization products of these polymers. Such polymers are described, for instance, in FR 2,162,025 and FR 2,280,361.

(6) Water-soluble polyamino amides prepared for example, by polycondensation of an acidic compound with a polyamine; these polyamino amides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound that is reactive with a bis-halohydrin, a bis-azetidinium, a bis-haloacyldiamine, a bis-alkyl halide, an epihalohydrin, a diepoxide or a bis-unsaturated derivative; the crosslinking agent may be used in an amount ranging from 0.025 to 0.35 mol per amine group of the polyamino amide; these polyamino amides can be alkylated or, if they contain at least one tertiary amine function, they can be quaternized. Such polymers are described, for instance, in FR 2,252,840 and FR 2,368,508. The polyamino amide derivatives resulting from the condensation of polyalkylene polyamines with polycarboxylic acids followed by alkylation with difunctional agents may also be used. Non-limiting mention may be made, for example, of adipic acid/dialkylaminohydroxyalkyl-dialkylene-triamine polymers wherein the alkyl radical comprises $C_1$–$C_4$ alkyl radicals, such as methyl, ethyl and propyl. Such polymers are described for instance in French Patent No. 1,583,363. Among these derivatives, non-limiting mention may be made for example, of the adipic acid/dimethylaminohydroxypropyl/diethylenetriamine polymers sold under the name Cartaretine F, F4 or F8 by the company Sandoz.

(7) The polymers obtained by reaction of a polyalkylene polyamine comprising two primary amine groups and at least one secondary amine group with a dicarboxylic acid chosen from diglycolic acid and saturated aliphatic $C_3$–$C_8$ dicarboxylic acids. The molar ratio between the polyalkylene polyamine and the dicarboxylic acid may range from 0.8/1 to 1.4/1; the polyamino amide resulting therefrom is reacted with epichlorohydrin in a molar ratio of epichlorohydrin relative to the secondary amine group of the polyamino amide ranging from 0.5/1 to 1.8/1. Such polymers are described for instance, in U.S. Pat. Nos. 3,227,615 and 2,961,347. Polymers of this type are sold for example, under the names "Hercosett 57," "PD 170," and "Delsette 101" by the company Hercules.

(8) Cyclopolymers of alkyldiallylamine and dialkyldiallylammonium, such as the homopolymers or copolymerscomprising, as main constituent of the chain, units of formulae (V) and (VI):

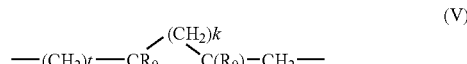
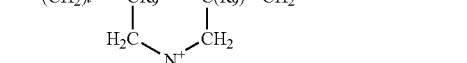

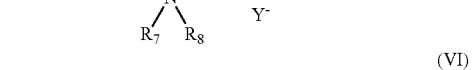
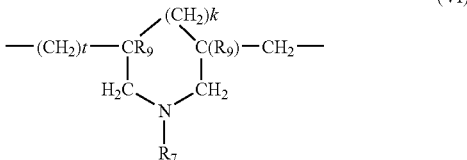

wherein:
k and t are equal to 0 or 1, provided that the sum k+t is equal to 1;

$R_9$ is chosen from hydrogen atoms and methyl radicals;

$R_7$ and $R_8$, which may be identical or different, are chosen from $C_1$–$C_8$ alkyl groups, hydroxyalkyl groups wherein the alkyl group comprises a $C_1$–$C_5$ alkyl group, amidoalkyl groups wherein the alkyl comprises a $C_1$–$C_4$ alkyl;

$R_7$ and $R_8$, together with the nitrogen atom to which they are attached, may also comprise heterocyclic groups such as piperidinyl and morpholinyl;

$R_7$ and $R_8$, which may be identical or different, for example, may comprise $C_1$–$C_4$ alkyl groups;

$Y^-$ comprises an organic or mineral anion such as bromide, chloride, acetate, borate, citrate, tartrate, bisulphate, bisulphite, sulphate and phosphate. These polymers are described for instance, in French Patent Nos. 2,080,759 and 2,190,406.

Among the polymers of group (8) defined above, non-limiting mention may be made for example, of the dimethyldiallylammonium chloride homopolymer sold under the name "Merquat 100" by the company Nalco, and its homologues of low weight-average molecular mass, as well as the copolymers of diallyldimethylammonium chloride and of acrylamide sold under the name "Merquat 550."

(9) The quaternary diammonium polymer comprising repeating units corresponding to the formula:

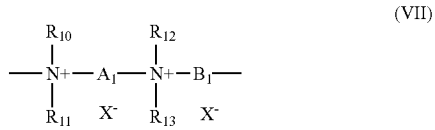

(VII)

wherein:

$R_{10}$, $R_{11}$, $R_{12}$ and $R_{13}$, which may be identical or different, may be chosen from $C_1$–$C_{20}$ aliphatic, alicyclic and arylaliphatic radicals and hydroxyalkylaliphatic radicals wherein the alkyl radical comprises a $C_1$–$C_4$ radical, or alternatively $R_{10}$, $R_{11}$, $R_{12}$ and $R_{13}$, together or separately, may comprise, with the nitrogen atoms to which they are attached, heterocycles optionally comprising a second hetero atom other than nitrogen, or alternatively $R_{10}$, $R_{11}$, $R_{12}$ and $R_{13}$ may be chosen from linear and branched $C_1$–$C_6$ alkyl radicals substituted with a group chosen from nitrile, ester, acyl and amide groups, —CO—O—$R_{14}$-D and —CO—NH—$R_{14}$-D wherein $R_{14}$ comprises an alkylene and D comprises a quaternary ammonium group;

$A_1$ and $B_1$ may be chosen from $C_2$–$C_{20}$ polymethylene groups which may be linear or branched, saturated or unsaturated, and which may contain, linked to or intercalated in the main chain, at least one entity chosen from aromatic rings oxygen atoms, sulphur atoms, sulphoxide, sulphone, disulphide, amino, alkylamino, hydroxyl, quaternary ammonium, ureido, amide and ester groups, and $X^{31}$ comprises an anion derived from mineral or organic acids;

$A_1$, $R_{10}$ and $R_{12}$ may also form, with the two nitrogen atoms to which they are attached, a piperazine ring;

in addition, if $A_1$ comprises a linear or branched, saturated or unsaturated alkylene or hydroxyalkylene radical, $B_1$ can also comprise a —$(CH_2)_n$—CO—D—OC—$(CH_2)_n$— group, wherein n ranges from 1 to 100, for instance, from 1 to 50, and D may be chosen from:

a) glycol residues of formula: —O—Z—O—, where Z may be chosen from linear and branched hydrocarbon-based radicals, —$(CH_2$—$CH_2$—$O)_x$—$CH_2$—$CH_2$—; and —$[CH_2$—$CH(CH_3)$—$O]_y$—$CH_2$—$CH(CH_3)$— groups, where x and y are integers ranging from 1 to 4, representing a defined and unique degree of polymerisation, or any number ranging from 1 to 4 representing an average degree of polymerization;

b) bis-secondary diamine residues such as a piperazine derivatives;

c) bis-primary diamine residues of formula: —NH—Y—NH—, where Y may be chosen from linear and branched hydrocarbon-based radicals, —$CH_2$—$CH_2$—S—S—$CH_2$—$CH_2$— radicals;

d) ureylene groups of formula: —NH—CO—NH—.

For example, $X^-$ may be an anion, such as chloride or bromide.

These polymers generally have a number-average molecular mass ranging from 1,000 to 100,000.

Polymers of group (9) are described for instance in French Patent Nos. 2,320,330; 2,270,846; 2,316,271; 2,336,434, and U.S. Pat. Nos. 2,413,907; 2,273,780; 2,375,853; 2,388,614; 2,454,547; 3,206,462; 2,261,002; 2,271,378; 3,874,870; 4,001,432; 3,929,990; 3,966,904; 4,005,193; 4,025,617; 4,025,627; 4,025,653; 4,026,945; and 4,027,020.

It is also possible to use polymers that comprise repeating units formula (VIII):

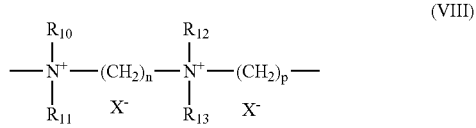

(VIII)

wherein $R_{10}$, $R_{11}$, $R_{12}$ and $R_{13}$, which may be identical or different, are chosen from $C_1$–$C_4$ alkyls and hydroxyalkyl radicals, n and p are integers ranging from 2 to 20 approximately, and $X^-$ comprises an anion derived from mineral or organic acids.

(10) Polyquaternary ammonium polymers comprising repeating units of formula (IX):

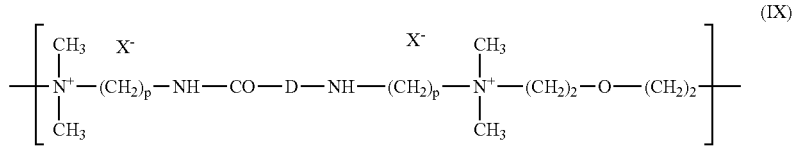

(IX)

wherein p is an integer ranging from about 1 to about 6, D may be chosen from nothing and —(CH$_2$)$_r$—CO— groups wherein r is a number equal to 4 or 7, and X$^-$ is an anion.

Polymers of group (10) may be prepared according to the processes described in U.S. Pat. Nos. 4,157,388; 4,702,906 and 4,719,282. They are also described for example, in patent application EP 122,324. Among these products, non-limiting mention may be made, for example, of "Mirapol A 15", "Mirapol AD1", "Mirapol AZ1" and "Mirapol 175" sold by the company Miranol.

(11) Quaternary polymers chosen from vinylpyrrolidone and vinylimidazole, such as, for example, the products sold under the names Luviquat FC 905, FC 550 and FC 370 by the company BASF.

(12) Polyamines such as Polyquart H sold by Cognis, which is given under the reference name "polyethylene glycol (15) tallow polyamine" in the CTFA dictionary.

(13) Crosslinked methacryloyloxy(C$_1$–C$_4$)alkyltri (C$_1$–C$_4$)alkylammonium salt polymers such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with a compound containing olefinic unsaturation, for example, methylenebisacrylamide. A crosslinked acrylamide/methacryloyloxyethyltrimethylammonium chloride copolymer, in a ratio of 20/80 by weight, in the form of a dispersion containing 50% by weight of the copolymer in mineral oil can be used, for example. This dispersion is sold under the name "Salcare® SC 92" by the company Ciba. A crosslinked methacryloyloxyethyltrimethylammonium chloride homopolymer containing about 50% by weight of the homopolymer in mineral oil or in a liquid ester can also be used. Such dispersions are sold under the names "Salcare® SC 95" and "Salcare® SC 96" by the company Ciba.

Other cationic polymers that can be used in the context of the present disclosure include polyalkyleneimines, for example polyethyleneimines, polymers comprising vinylpyridine, and vinylpyridinium units, condensates of polyamines and of epichlorohydrin, quaternary polyureylenes and chitin derivatives.

Among all the cationic polymers that may be used in the context of the present disclosure, non-limiting mention may be made of the polymers of groups (1), (8), (9), (10) and (13), for example the polymers comprising repeating units of formulae (W) and (U):

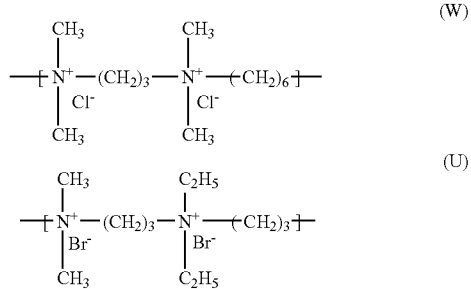

for example, polymers of formula (W) with a molecular weight, determined by gel permeation chromatography, ranging from 9,500 to 9,900; and polymers of formula (U) with a molecular weight, determined by gel permeation chromatography, at about 1,200.

The cationic polymer may be present in the cosmetic composition according to the present disclosure in an amount ranging from 0.01% to 20% by weight, relative to the total weight of the cosmetic composition, for instance ranging from 0.1% to 10% by weight, relative to the total weight of the cosmetic composition.

The cosmetically acceptable medium generally comprises water, or a mixture of water and at least one common organic solvent. Among the solvents that are suitable for use, non-limiting mention may be made of, for example, alcohols such as ethyl alcohol, isopropyl alcohol, benzyl alcohol and phenylethyl alcohol, or glycols or glycol ethers, for instance ethylene glycol monomethyl ether, monoethyl ether or monobutyl ether, propylene glycol and ethers thereof, for instance propylene glycol monomethyl ether, butylene glycol, dipropylene glycol and diethylene glycol alkyl ethers, for instance diethylene glycol monoethyl ether or monobutyl ether, or alternatively polyols, for instance glycerol. Polyethylene glycols and polypropylene glycols, and mixtures of all these compounds, may also be used as solvent.

The at least one common solvent, if present, can be in the cosmetic composition in an amount ranging from 1% to 40% by weight, for example, from 5% to 30% by weight, relative to the total weight of the cosmetic composition.

The pH of the cosmetic composition in accordance with the present disclosure may range from about 3 to 12, for example, from about 5 to about 11. The pH may be adjusted to the desired value by means of acidifying or basifying agents. Non-limiting examples of acidifying agents that may be mentioned include mineral or organic acids, for instance hydrochloric acid, orthophosphoric acid, sulphuric acid, carboxylic acids, for instance acetic acid, tartaric acid, citric acid and lactic acid, and sulphonic acids. Non-limiting examples of basifying agents that may be mentioned include aqueous ammonia, alkaline carbonates, alkanolamines such as monoethanolamine, diethanolamine and triethanolamine and derivatives thereof, sodium hydroxide, potassium hydroxide and the compounds of formula (A):

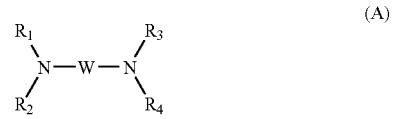

wherein W comprises a propylene residue optionally substituted with an entity chosen from a hydroxyl group and C$_1$–C$_6$ alkyl radicals; R$_1$, R$_2$, R$_3$ and R$_4$, which may be identical or different, are chosen from hydrogen atoms, and C$_1$–C$_6$ alkyl and C$_1$–C$_6$ hydroxyalkyl radicals.

According to one aspect of the present disclosure, the cosmetic composition may comprise, in addition to the at least one fluorescent dye, at least one additional non-fluorescent direct dyes of nonionic, cationic or anionic nature, which may be chosen, for example, from nitrobenzene dyes. For example, the following red or orange nitrobenzene direct dyes can be suitable for use:

1-hydroxy-3-nitro-4-N-(γ-hydroxypropyl)aminobenzene,
N-(β-hydroxyethyl)amino-3-nitro-4-aminobenzene,
1-amino-3-methyl-4-N-(β-hydroxyethyl)amino-6-nitrobenzene,
1-hydroxy-3-nitro-4-N-(β-hydroxyethyl)aminobenzene,
1,4-diamino-2-nitrobenzene,
1-amino-2-nitro-4-methylaminobenzene,
N-(β-hydroxyethyl)-2-nitro-para-phenylenediamine, 1-amino-2-nitro-4-(β-hydroxyethyl)amino-5-chlorobenzene,
2-nitro-4-aminodiphenylamine,
1-amino-3-nitro-6-hydroxybenzene,
1-(β-aminoethyl)amino-2-nitro-4-(β-hydroxyethyloxy)benzene,
1-(β,γ-dihydroxypropyl)oxy-3-nitro-4-(β-hydroxyethyl)aminobenzene,
1-hydroxy-3-nitro-4-aminobenzene,
1-hydroxy-2-amino-4,6-dinitrobenzene,
1-methoxy-3-nitro-4-(β-hydroxyethyl)aminobenzene,
2-nitro-4'-hydroxydiphenylamine and
1-amino-2-nitro-4-hydroxy-5-methylbenzene.

The cosmetic composition in accordance with the present disclosure may also comprise, in addition to, or instead of the above described nitrobenzene dyes, at least one additional direct dye chosen from yellow, green-yellow, blue and violet nitrobenzene dyes, nitrobenzene dyes, azo dyes, anthraquinone dyes, naphthoquinone dyes, benzoquinone dyes, phenothiazine dyes, indigoid dyes, xanthene dyes, phenanthridine dyes, phthalocyanin dyes, triarylmethane-based dyes, and mixtures thereof.

The at least one additional direct dye may be for example, chosen from basic dyes, among which non-limiting mention may be made of, for example, the dyes known in the Color Index, 3rd edition, under the names "Basic Brown 16," "Basic Brown 17," "Basic Yellow 57," "Basic Red 76," "Basic Violet 10," "Basic Blue 26" and "Basic Blue 99", or chosen from acidic direct dyes, among which non-limiting mention may be made of, for example, the dyes known in the Color Index, 3rd edition, under the names "Acid Orange 7," "Acid Orange 24," "Acid Yellow 36," Acid Red 33," "Acid Red 184," "Acid Black 2," "Acid Violet 43" and "Acid Blue 62", or chosen from cationic direct dyes such as those described in WO 95/01772, WO 95/15144 and EP 714,954, the content of which is incorporated herein by reference.

Among the at least one additional yellow and green-yellow nitrobenzene direct dyes, non-limiting mention may be made, for example, of the compounds chosen from:
1-β-hydroxyethyloxy-3-methylamino-4-nitrobenzene,
1-methylamino-2-nitro-5-(β,γ-dihydroxypropyl)oxybenzene,
1-(β-hydroxyethyl)amino-2-methoxy-4-nitrobenzene,
1-(β-aminoethyl)amino-2-nitro-5-methoxybenzene,
1,3-di(β-hydroxyethyl)amino-4-nitro-6-chlorobenzene,
1-amino-2-nitro-6-methylbenzene,
1-(β-hydroxyethyl)amino-2-hydroxy-4-nitrobenzene,
N-(β-hydroxyethyl)-2-nitro-4-trifluoromethylaniline,
4-(β-hydroxyethyl)amino-3-nitrobenzenesulphonic acid,
4-ethylamino-3-nitrobenzoic acid,
4-(β-hydroxyethyl)amino-3-nitrochlorobenzene,
4-(β-hydroxyethyl)amino-3-nitromethylbenzene,
4-(β,γ-dihydroxypropyl)amino-3-nitrotrifluoromethylbenzene,
1-(β-ureidoethyl)amino-4-nitrobenzene,
1,3-diamino-4-nitrobenzene,
1-hydroxy-2-amino-5-nitrobenzene,
1-amino-2-[tris(hydroxymethyl)methyl]amino-5-nitrobenzene,
1-(β-hydroxyethyl)amino-2-nitrobenzene and
4-(β-hydroxyethyl)amino-3-nitrobenzamide.

Among the at least one additional blue or violet nitrobenzene direct dye that may be used, non-limiting mention may be made, for example, of the compounds chosen from:
1-(β-hydroxyethyl)amino-4-N,N-bis(β-hydroxyethyl)amino-2-nitrobenzene,
1-(γhydroxypropyl)amino-4,N,N-bis(β-hydroxyethyl)amino-2-nitrobenzene,
1-(β-hydroxyethyl)amino-4-(N-methyl-N-β-hydroxyethyl)amino-2-nitrobenzene,
1-(β-hydroxyethyl)amino-4-(N-ethyl-N-β-hydroxyethyl)amino-2-nitrobenzene,
1-(β,γ-dihydroxypropyl)amino-4-(N-ethyl-N-β-hydroxyethyl)amino-2-nitrobenzene, 2-nitroparaphenylenediamines of the formula:

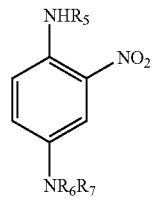

wherein:
$R_6$ may be chosen from $C_1$–$C_4$ alkyl radicals and β-hydroxyethyl, β-hydroxypropyl, and γ-hydroxypropyl radicals;
$R_5$ and $R_7$, which may be identical or different, may be chosen form β-hydroxyethyl, β-hydroxypropyl, γ-hydroxypropyl and β,γ-dihydroxypropyl radicals, wherein at least one of the radicals $R_6$, $R_7$ and $R_5$ comprise a γ-hydroxypropyl radical and wherein $R_6$ and $R_7$ may not simultaneously comprise a β-hydroxyethyl radical when $R_6$ is a γ-hydroxypropyl radical, such as those described in FR 2,692,572.

When present in the cosmetic composition, the at least one additional direct dye may be present in an amount ranging from about 0.0005% to about 12% by weight, relative to the total weight of the composition, and for example, from about 0.005% to about 6% by weight, relative to the total weight of the composition.

When it is intended for oxidation dyeing, the cosmetic composition in accordance with the present disclosure comprises, in addition to the at least one fluorescent compound, at least one oxidation base chosen from oxidation bases conventionally used for oxidation dyeing and among which non-limiting mention may be made of, for example, para-phenylenediamines, bis(phenyl)alkylenediamines, para-amino-phenols, ortho-aminophenols, heterocyclic bases, and the addition salts thereof with an acid or with an alkaline agent.

Among the para-phenylenediamines that may be used, non-limiting mention may be made of, for example, para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'- aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4'-aminophenyl-1-(3-hydroxy) pyrrolidine, and the addition salts thereof with an acid or with an alkaline agent. For instance, the para-phenylenediamines mentioned above, may be chosen from para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-β-acetylaminoethyloxy-para-phenylenediamine, and the addition salts thereof with an acid or with an alkaline agent.

Among the bis(phenyl)alkylenediamines that may be used, non-limiting mention may be made of, for example, N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl) ethylenediamine, 1,8-bis(2,5-diaminophenoxy)-3,5-dioxaoctane, and the addition salts thereof with an acid or with an alkaline agent.

Among the para-aminophenols that may be used, non-limiting mention may be made of, for example, para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, and the addition salts thereof with an acid or with an alkaline agent.

Among the ortho-aminophenols that may be used, non-limiting mention may be made of, for example, 2-aminophenol, 2-amino-5-methylphenol, 2-amino-6-methylphenol, 5-acetamido-2-aminophenol, and the addition salts thereof with an acid or with an alkaline agent.

Among the heterocyclic bases that may be used, non-limiting mention may be made of, for example, pyridine derivatives, pyrimidine derivatives, pyrazole derivatives, and the addition salts thereof with an acid or with an alkaline agent.

When they are used, the at least one oxidation base may be present in the cosmetic composition in an amount ranging from about 0.0005% to about 12% by weight, relative to the total weight of the composition, for example, ranging from about 0.005% to about 6% by weight, relative to the total weight of the composition.

When it is intended for oxidation dyeing, the cosmetic composition in accordance with the present disclosure may also comprise, in addition to the at least one fluorescent dye and the at least one oxidation base, at least one coupler so as to modify or to enrich with glints the shades obtained using the at least one fluorescent dye and the at least one oxidation base.

The couplers that may be used in the cosmetic composition in accordance with the present disclosure may be chosen from couplers conventionally used in oxidation dyeing, among which non-limiting mention may be made of, for example meta-phenylenediamines, meta-aminophenols, meta-diphenols, heterocyclic couplers, and the addition salts thereof with an acid or with an alkaline agent. For further example, the at least one coupler may be chosen from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, (α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole, 6-methylpyrazolo[1,5-a]benzimidazole, and the addition salts thereof with an acid or with an alkaline agent.

When present in the cosmetic composition, the at least one coupler may be present, for example, in an amount ranging from about 0.0001% to about 10% by weight, for instance ranging from about 0.005% to about 5% by weight, relative to the total weight of the composition.

In general, the addition salts with an acid that may be used in the context of the cosmetic compositions of the present disclosure, e.g. with the oxidation bases and couplers, may be chosen for example, from hydrochlorides, hydrobromides, sulphates, citrates, succinates, tartrates, tosylates, benzenesulphonates, lactates and acetates.

The addition salts with an alkaline agent that may be used in the context of the cosmetic compositions of the present disclosure, e.g. with the oxidation bases and couplers, may be chosen for example, from the addition salts with alkali metals or alkaline-earth metals, with ammonia and with organic amines, including alkanolamines and the compounds of formula (VIII).

The cosmetic composition as disclosed herein may also comprise various conventionally used adjuvants, such as anionic, cationic, nonionic, amphoteric and zwitterionic surfactants and mixtures thereof, anionic, cationic, nonionic, amphoteric and zwitterionic polymers other than those of the invention, and mixtures thereof, mineral thickeners, antioxidants, penetrating agents, sequestering agents, fragrances, buffers, dispersants, conditioners, for instance cations, volatile or non-volatile, modified or unmodified silicones, film-forming agents, ceramides, preserving agents, stabilizers and opacifiers.

Among the thickeners that may be used, non-limiting mention made of, for example, thickening systems based on associative polymers that are known to those skilled in the art, and such as those of the nonionic, anionic, cationic and amphoteric nature.

When at least one surfactant is present in the cosmetic composition, for instance of the nonionic, anionic and amphoteric type, it may be present in an amount ranging from about 0.01% to about 30% by weight, relative to the weight of the composition.

Needless to say, a person skilled in the art will take care to select any of the optional additional compounds discussed herein, such that the advantageous properties intrinsically associated with the cosmetic composition in accordance with the invention are not, or are not substantially, adversely affected by the envisaged addition.

The cosmetic composition according to the present disclosure may be in various forms, such as in the form of liquids, shampoos, creams or gels, or in any other suitable form. According to one aspect of the present disclosure, the cosmetic composition is in the form of a lightening dye shampoo and further comprisesa cosmetically acceptable aqueous medium.

In the cosmetic composition according to the present disclosure, when at least one oxidation base is used, optionally in the presence of at least one coupler, or when at least one fluorescent dye is used as a lightening direct dye, then the composition in accordance with the present disclosure may also contain at least one oxidizing agent.

The oxidizing agent may be chosen, for example, from hydrogen peroxide, urea peroxide, alkali metal bromates, persalts such as perborates and persulphates, and enzymes such as peroxidases and two-electron and four-electron oxidoreductases. For example, the at least one oxidizing agent may be chosen from hydrogen peroxide and enzymes.

One aspect of the present disclosure is the method of use, for dyeing human keratin materials with a lightening effect, of a cosmetic composition comprising, in a cosmetically acceptable medium, at least one fluorescent dye that is soluble in the medium, and at least one cationic polymer with a charge density of at least 1 meq/g. In the context of this aspect of the disclosure, the at least one fluorescent compound may be chosen, for example, from fluorescent dyes belonging to the following families: naphthalimides; cationic and non-cationic coumarins; xanthenodiquinolizines, such as sulphorhodamines; azaxanthenes; naphtholactams; azlactones; oxazines; thiazines; dioxazines; monocationic and polycationic fluorescent dyes of azo, azomethine and methine type, alone or as mixtures.

For example, non-limiting mention may be made of compounds of formulae F1, F2 and F3 detailed above.

It is similarly possible to use the compounds of structure (F4) below:

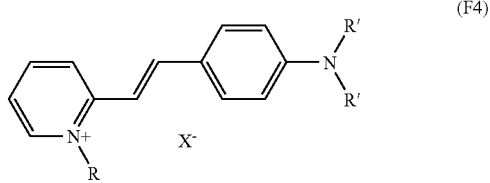

(F4)

wherein R may be chosen from methyl and ethyl radicals; R' comprises methyl radicals, and X⁻ comprises anions such as chloride, iodide, sulphate, methosulphate, acetate and perchlorate. An example of a compound of this type that may be mentioned is the Photosensitizing Dye NK-557 sold by the company Ubichem, wherein R comprises an ethyl radical, R' comprises methyl radicals and X⁻ comprises iodide.

Everything that has been described previously regarding the natures and contents of the various additives present in the cosmetic composition remains valid and will not be repeated in this section.

According to the present disclosure, the term "human keratin materials" means the skin, the hair, the nails, the eyelashes and the eyebrows, for example, dark skin and artificially colored and pigmented hair.

As used herein, the term "dark skin" means a skin whose lightness L* measured in the CIEL L*a*b* system is less than or equal to 45, for example, less than or equal to 40, given that L*=0 is equivalent to black and L*=100 is equivalent to white. The skin types corresponding to this lightness include African skin, afro-American skin, hispano-American skin, Indian skin and North African skin.

As used herein, the expression "artificially dyed or pigmented hair" means hair whose tone height is less than or equal to 6, i.e., dark blond, for example, less than or equal to 4, i.e., chestnut-brown.

The lightening of the hair is evaluated by the "tone height," which characterizes the degree or level of lightening. The notion of "tone" is based on the classification of the natural shades, one tone separating each shade from the shade immediately following or preceding it. This definition and the classification of the natural shades are well known to hairstyling professionals and are published in the book *Sciences des traitements capillaires [Hair treatment sciences]* by Charles Zviak, 1988, published by Masson, pp. 215 and 278.

The tone heights range from 1 (black) to 10 (light blond), wherein one unit corresponds to one tone; the higher the figure, the lighter the shade.

Another aspect of the present disclosure thus concerns a process for dyeing human keratin fibers with a lightening effect, which comprises performing the following steps:

a) the cosmetic composition according to the present disclosure is applied to the keratin fibers, for a time that is sufficient to develop the desired coloration and lightening, b) the fibers are optionally rinsed, c) the fibers are optionally washed with shampoo and rinsed, d) the fibers are dried or are left to dry.

Another aspect of the present disclosure is also a process for coloring dark skin with a lightening effect, wherein the cosmetic composition described herein is applied to the skin and the skin is then dried or is left to dry. For example, the cosmetic composition may not have to comprise any oxidation base or coupler and may not need to be used in the presence of an oxidizing agent.

Everything that has been described previously regarding the various constituent components of the cosmetic composition remains valid, and reference may be made thereto.

For further example, the processes according to the present disclosure are suitable for treating human keratin fibers, such as artificially colored or pigmented hair, or alternatively dark skin.

The fibers that may be treated with the process according to the present disclosure, for instance, may have a tone height of less than or equal to 6, i.e., dark blond such as, less than or equal to 4, i.e., chestnut-brown.

Furthermore, a dark skin capable of being treated in accordance with the invention has a lightness L*, measured in the CIEL L*a*b* system, of less than or equal to 45, such as less than or equal to 40.

According to a first aspect of the present disclosure, the process of dyeing fibers with a lightening effect is performed with a cosmetic composition that does not comprise any oxidation dyes or coupler, and in the absence of oxidizing agent.

According to a second aspect of the present disclosure, the process of dyeing fibers with a lightening effect is performed with a cosmetic composition that does not comprise any oxidation dyes or coupler, but in the presence of at least one oxidizing agent.

According to another aspect of these dyeing processes according to the present disclosure, at least one cosmetic composition as defined above is applied to the fibers, such as the hair, for a time that is sufficient to develop the desired coloration and lightening, after which the fibers are rinsed, optionally washed with shampoo, rinsed again and dried.

According to yet another aspect of the dyeing processes in accordance with the present disclosure, at least one cosmetic composition as defined above is applied to the fibers, such as the hair, without final rinsing.

According to still yet another aspect of the dyeing process in accordance with the present disclosure, the dyeing process may comprise a preliminary step that comprises separately storing, at least one cosmetic composition according to the present disclosure optionally comprising at least one oxidation base and/or at least one coupler, and, separately storing at least one composition comprising, in a cosmetically acceptable medium, at least one oxidizing agent, and then in mixing the separately stored compositions together at the time of use, after which the mixture is applied to the keratin fibers, such as the hair, for a time that is sufficient to develop the desired coloration, after which the fibers are rinsed, optionally washed with shampoo, rinsed again and dried.

The time required to develop the coloration and/or to obtain the lightening effect on the fibers, such as the hair, may range from about 5 to about 60 minutes, for instance, from about 5 to about 40 minutes.

The temperature required to develop the coloration and/or to obtain the lightening effect ranges from about 15° C. to about 80° C., for instance from about 15 to about 40° C., and for example, about room temperature.

Yet another aspect of the invention is a multi-compartment device or "kit" for dyeing keratin fibers, such as the hair, with a lightening effect, comprising at least one compartment containing a cosmetic composition according to the present disclosure, and at least one other compartment containing a composition comprising at least one oxidizing agent. This device may be equipped with a means for applying the desired mixture to the fibers, such as the devices described in patent FR 2,586,913.

The cosmetic composition according to the present disclosure, if it is used to treat keratin fibers, for example such as chestnut-brown hair, the following reflectance results are possible: If the reflectance of the hair is measured when it is irradiated with visible light in the wavelength range from about 400 to about 700 nanometres, and if the curves of reflectance as a function of the wavelength are compared for hair treated with the cosmetic composition of the present disclosure and untreated hair, it is found that the reflectance curve corresponding to the treated hair, in a wavelength range from about 500 to about 700 nanometres, is higher than that corresponding to the untreated hair. As used herein in the context of reflectance curves, the term "higher than" means a difference of at least 0.05%, for instance of at least 0.1% of reflectance. This means that, in the wavelength range from about 500 to about 700 nanometres, for instance from about 540 to about 700 nanometres, there is at least one range in which the reflectance curve corresponding to the treated hair is higher than the reflectance curve corresponding to the untreated hair. However, it is noted that there may be, within the wavelength range from about 500 to about 700 nanometres, for instance from about 540 to about 700 nanometres, at least one range of the reflectance curve corresponding to the treated fibers may be either superimposable on, or lower than the reflectance curve corresponding to the untreated fibers.

For example, the wavelength at which the difference is maximal between the reflectance curve for the treated hair and that for the untreated hair may be in the wavelength range from about 500 to about 650 nanometres, for instance ranging from about 550 to about 620 nanometres.

In addition, for example, the cosmetic composition according to the present disclosure is capable of lightening the hair and the skin in a shade which, measured in the CIEL L*a*b* system, has a variable b* of greater than or equal to 6, with a ratio of b*/(absolute value of a*) of greater than 1.2 according to the selection test described below.

Selection Test

The cosmetic composition as disclosed herein is applied to chestnut-brown keratin fibers, such as the hair, at a rate of 10 grams of composition per 1 gram of chestnut-brown fibers. The composition is spread on so as to cover all of the fibers. The composition is left to act for 20 minutes at room temperature ranging from about 20 to about 25° C. The fibers are then rinsed with water and then washed with a shampoo based on lauryl ether sulphate. They are then dried. The spectrocolorimetric characteristics of the fibers are then measured in order to determine the L*a*b* coordinates. In the CIEL L*a*b* system, a* and b* indicate two color axes: a* indicates the green/red color axis (+a* is red, −a* is green) and b* indicates the blue/yellow color axis (+b* is yellow and −b* is blue); values close to zero for a* and b* correspond to grey shades.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements. The following examples are intended to illustrate the invention without limiting the scope as a result. The percentages are given on a weight basis.

EXAMPLES

Fluorescent Compound

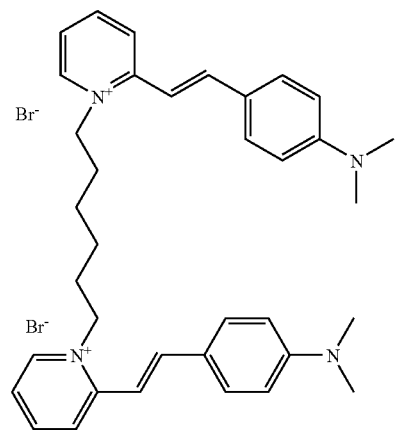

93 g of 2-picoline were reacted with 120 g of 1,6-dibromohexane in dimethylformamide at 110° C. for 5 hours.

The precipitated product was recovered and filtered off.

109 g of the product obtained above were dissolved in methanol and 82.82 g of p-dimethylaminobenzaldehyde were added in two portions, in the presence of pyrrolidine.

The mixture was then left for 30 minutes.

The product was recovered in precipitated form.

Analysis by mass spectroscopy: 266.

Elemental analysis: C: 62.43%; H: 6.40%; Br: 23.07%; N: 8.09%.

The formula was as follows: $C_{36}H_{44}N_4 \cdot 2Br$.

| Compositions | | |
|---|---|---|
| Composition | 1 | 2 |
| Fluorescent compound | 1% | 1% |
| Merquat 100 (*) | 1% | — |
| Salcare SC95 (**) | — | 1% |
| Distilled water | qs 100% | qs 100% |

(*) dimethyldiallylammonium chloride homopolymer (Nalco)
(**) crosslinked methacryloyloxyethyltrimethylammonium chloride homopolymer (Ciba)

Coloration

Each composition was applied to a lock of natural chestnut-brown hair (tone height 4) and left on the hair for 20 minutes.

The locks were then rinsed and dried under a hood for 30 minutes.

A marked lightening effect is obtained on the locks that were thus treated.

What is claimed is:

1. A cosmetic composition comprising, in a cosmetically acceptable medium, at least one fluorescent dye that is soluble in the medium and at least one cationic polymer with a charge density of at least 1 meq/g;

with the proviso that the at least one fluorescent dye is not 2-[2-(4-dialkylamino)phenylethenyl]-1-alkylpyridinium wherein the alkyl radical of the pyridinium nucleus is chosen from methyl and ethyl radicals and wherein the radical of the benzene nucleus comprises a methyl radical, and wherein the counterion is a halide; and wherein the at least one fluorescent dye is chosen from:

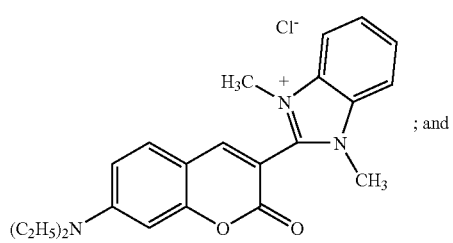

(F1)

; and

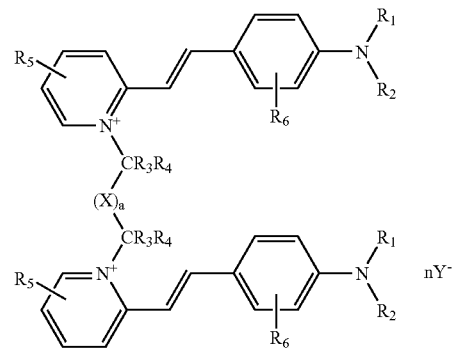

(F3)

wherein;

$R_1$ and $R_2$, which may be identical or different, are chosen from:
hydrogen atoms;
linear and branched alkyl radicals comprising from 1 to 10 carbon atoms, optionally interrupted with at least one entity chosen from hetero atoms and groups comprising at least one hetero atom, and optionally substituted with at least one entity chosen from hetero atoms, groups comprising at least one hetero atom, and halogen atoms;
aryl and arylalkyl radicals, wherein the aryl groups comprise 6 carbon atoms and the alkyl radicals comprise from 1 to 4 carbon atoms; the aryl radical is optionally substituted with at least one linear or branched alkyl radical comprising from 1 to 4 carbon atoms optionally interrupted with at least one entity chosen from hetero atoms and groups comprising at least one hetero atom and optionally substituted with at least one entity chosen from hetero atoms, groups comprising at least one hetero atom, and halogen atoms;

$R_1$ and $R_2$ may optionally be linked so as to form a heterocycle with the nitrogen atom and may further comprise at least one hetero atom, wherein the heterocycle may be optionally substituted with at least one linear or branched alkyl radical optionally interrupted with at least one entity chosen from hetero atoms and groups comprising at least one hetero atom, and/or optionally substituted with at least one entity chosen from hetero atoms, groups comprising at least one hetero atom, and halogen atoms;

$R_1$ or $R_2$ may also optionally be included in a heterocycle comprising the nitrogen atom and one of the carbon atoms of the phenyl group comprising the nitrogen atom;

$R_3$ and $R_4$, which may be identical or different, are chosen from hydrogen atoms and alkyl radicals comprising from 1 to 4 carbon atoms;

$R_5$, which may be identical or different, is chosen from hydrogen atoms, halogen atoms, and linear and branched alkyl radicals comprising from 1 to 4 carbon atoms, optionally interrupted with at least one hetero atoms;

$R_6$, which may be identical or different, is chosen from hydrogen atoms; halogen atoms; and linear and branched alkyl radicals comprising from 1 to 4 carbon atoms, optionally substituted with at least one entity chosen from hetero atoms, groups comprising at least one hetero atom, and halogen atoms, and/or interrupted with at least one entity chosen from hetero atoms and groups comprising at least one hetero atom;

X is chosen from:
- linear and branched alkyl radicals comprising from 1 to 14 carbon atoms and alkenyl radicals comprising from 2 to 14 carbon atoms, optionally interrupted with at least one entity chosen from hetero atoms and groups substituted with at least one hetero atom, and/or optionally substituted with at least one entity chosen from hetero atoms, groups containing at least one hetero atom, and halogen atoms;
- 5- and 6-membered heterocyclic radicals optionally substituted with at least one entity chosen from linear and branched alkyl radicals comprising from 1 to 14 carbon atoms, optionally substituted with at least one hetero atom; linear and branched aminoalkyl radicals comprising from 1 to 4 carbon atoms, optionally substituted with at least one hetero atom; and halogen atoms;
- fused and non-fused aromatic and diaromatic radicals, optionally separated with an alkyl radical comprising from 1 to 4 carbon atoms, wherein the aromatic and diaromatic radicals are optionally substituted with at least one entity chosen from halogen atoms and alkyl radicals comprising from 1 to 10 carbon atoms optionally substituted and/or interrupted with at least one hetero atom and/or group comprising at least one hetero atom;
- dicarbonyl radicals;

the group X optionally comprising at least one cationic charge;
a is equal to 0 or 1;
Y$^-$, which may be identical or different, is chosen from organic and mineral anions; and
n is an integer ranging from 2 to the number of cationic charges present in the fluorescent dye.

2. The cosmetic composition according to claim 1, wherein the at least one fluorescent dye is in the orange range.

3. The cosmetic composition according to claim 1, wherein the at least one fluorescent dye provides a reflectance maximum that is in the wavelength range from about 500 to about 650 nanometers.

4. The cosmetic composition according to claim 3, wherein the at least one fluorescent dye provides a reflectance maximum that is in the wavelength range from about 550 to about 620 nanometers.

5. The cosmetic composition according to claim 1, wherein $R_1$ and $R_2$, which may be identical or different, are chosen from linear and branched alkyl radicals comprising from 1 to 4 carbon atoms optionally interrupted with at least one entity chosen from hetero atoms and groups comprising at least one hetero atom, and optionally substituted with at least one entity chosen from hetero atoms, groups comprising at least one hetero atom, and halogen atoms.

6. The cosmetic composition according to claim 1, wherein the heterocycle formed by $R_1$ and $R_2$ linked with the nitrogen atom is substituted with at least one linear or branched alkyl radical comprising from 1 to 4 carbon atoms, wherein the alkyl radical is optionally interrupted with at least one entity chosen from hetero atoms and groups comprising at least one hetero atom, and optionally substituted with at least one entity chosen from hetero atoms, groups comprising at least one hetero atom, and halogen atoms.

7. The cosmetic composition according to claim 1, wherein the at least one fluorescent dye is present in an amount ranging from about 0.01% to about 20% by weight, relative to the total weight of the cosmetic composition.

8. The cosmetic composition according to claim 7, wherein the at least one fluorescent dye is present in an amount ranging from about 0.05% to about 10% by weight, relative to the total weight of the cosmetic composition.

9. The cosmetic composition according to claim 8, wherein the at least one fluorescent dye is present in an amount ranging from about 0.1% to about 5% by weight, relative to the total weight of the cosmetic composition.

10. The cosmetic composition according to claim 1, wherein the at least one cationic polymer is chosen from linear and random homopolymers and copolymer, grafted or in block form, and further comprises at least one cationic group and/or at least one group that can be ionized into a cationic group, chosen from primary, secondary, tertiary and quaternary amine groups forming part of the main chain of the polymer or borne by a side substituent directly attached thereto.

11. The cosmetic composition according to claim 10, wherein the at least one cationic polymer is chosen from:

(1) Homopolymers and copolymers derived from acrylic and methacrylic esters and amides, and comprising at least one unit chosen from formulae (I), (II), (III) and (IV):

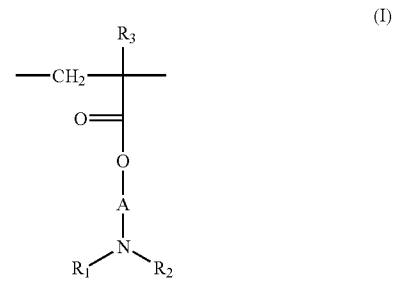

(I)

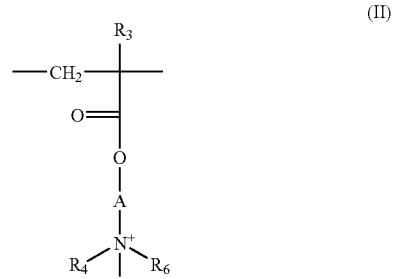

(II)

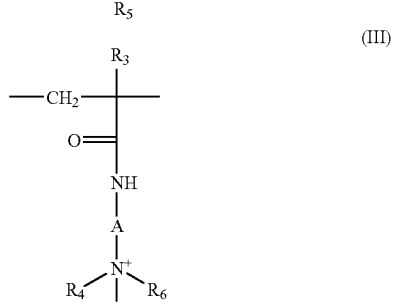

(III)

-continued

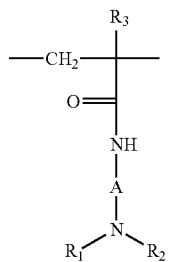

(IV)

wherein:
R$_3$, which may be identical or different, is chosen from hydrogen atoms and CH$_3$ radicals;
A, which may be identical or different, is chosen from linear and branched C$_1$–C$_6$ alkyl groups and hydroxyalkyl groups wherein the alkyl is a C$_1$–C$_4$ alkyl;
R$_4$, R$_5$ and R$_6$, which may be identical or different, are chosen from C$_1$–C$_{18}$ alkyl groups and benzyl radicals;
R$_1$ and R$_2$, which may be identical or different, are chosen from hydrogen atoms and C$_1$–C$_6$ alkyl groups;

(2) cellulose ether derivatives comprising quaternary ammonium groups;

(3) cationic cellulose derivatives;

(4) cationic polysaccharides of plant origin;

(5) polymers comprising piperazinyl units and linear and branched divalent alkyl and hydroxyalkyl radicals, optionally interrupted with at least one entity chosen from oxygen, sulphur, and nitrogen atoms; and aromatic and heterocyclic rings, and the oxidation and quaternization products of these polymers;

(6) optionally crosslinked, water-soluble polyamino amides;

(7) polymers obtained by reacting a polyalkylenepolyamine comprising two primary amine groups and at least one secondary amine group with a dicarboxylic acid;

(8) alkyldiallylamine and dialkyldiallylammonium cyclopolymers, in the form of homopolymers and copolymers comprising, as the main constituent of the chain, units corresponding to formula (V) or (VI):

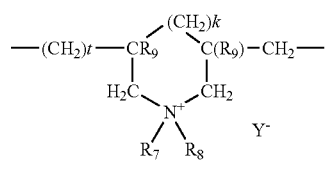

(V)

(VI)

wherein k and t are equal to 0 or 1, provided that the sum of k+t is equal to 1; R$_9$ is chosen from hydrogen atoms and methyl radicals; R$_7$ and R$_8$, which may be identical or different, are chosen from C$_1$–C$_8$ alkyl groups, hydroxyalkyl groups wherein the alkyl group is a C$_1$–C$_5$ alkyl group, and amidoalkyl groups wherein the alkyl is a C$_1$–C$_4$ alkyl; R$_7$ and R$_8$ can also form, together with the nitrogen atom to which they are attached, a heterocyclic group; Y$^-$ is chosen from organic and mineral anions;

(9) quaternary diammonium polymers comprising repeating units of formula (VII):

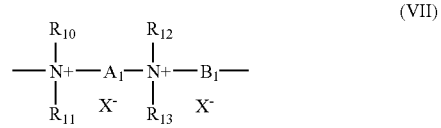

(VII)

wherein:
R$_{10}$, R$_{11}$, R$_{12}$ and R$_{13}$, which may be identical or different, are chosen from linear, branched and cyclic, saturated, unsaturated and aromatic C$_1$–C$_{20}$ hydrocarbon-based radicals; linear and branched hydroxyalkyl radicals, wherein the alkyl is C$_1$–C$_4$ alkyl; linear and branched C$_1$–C$_6$ alkyl radicals substituted with an entity chosen from nitrile, ester, acyl and amide groups, and —CO—O—R$_{14}$—D and —CO—NH—R$_{14}$—D groups, wherein
R$_{14}$ comprises an alkyl radical and D comprises a quaternary ammonium group; or wherein R$_{10}$, R$_{11}$, R$_{12}$ and R$_{13}$, together or separately, with the nitrogen atoms to which they are attached, form heterocycles optionally comprising a second hetero atom other than nitrogen;

A$_1$ and B$_1$ are chosen from linear and branched, saturated and unsaturated C$_2$–C$_{20}$ radicals optionally substituted and optionally interrupted with at least one entity chosen from aromatic rings, oxygen atoms, sulphur atoms, and groups comprising at least one hetero atom chosen from oxygen and sulphur atoms;

X$^-$ is chosen from organic and mineral anions;

A$_1$, R$_{10}$ and R$_{12}$ may optionally form a piperazine ring with the two nitrogen atoms to which they are attached; and, if A$_1$ is chosen from linear and branched, saturated and unsaturated alkylene and hydroxyalkylene radicals, B$_1$ optionally comprises —(CH$_2$)$_n$—CO—D—OC—(CH$_2$)$_n$— wherein n ranges from 1 to 100, and D is chosen from glycol, bis-secondary diamine, bis-primary diamine and ureylene residue;

(10) polyquaternary ammonium polymers comprising repeating units of formula (IX):

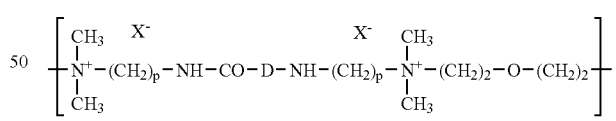

(IX)

wherein p is an integer ranging from 1 to 6, D, when it is present, comprises —(CH$_2$)$_r$—CO— groups wherein r is equal to 4 or 7, and X$^-$ is chosen from organic and mineral anions;

(11) quaternary polymers of vinylpyrrolidone and of vinylimidazole;

(12) polyamines; and

(13) crosslinked polymers of methacryloyloxy(C$_1$–C$_4$) alkyltri(C$_1$–C$_4$)alkylammonium salts.

12. The cosmetic composition according to claim 1, wherein the at least one cationic polymer is present in an amount ranging from about 0.01% to about 20% by weight, relative to the total weight of the cosmetic composition.

13. The cosmetic composition according to claim 9, wherein the at least one cationic polymer is present in an amount ranging from about 0.1% to about 10% by weight, relative to the total weight of the cosmetic composition.

14. The cosmetic composition according to claim 1, further comprising at least one surfactant chosen from nonionic, anionic and amphoteric surfactants.

15. The cosmetic composition according to claim 14, wherein the at least one surfactant is present in an amount ranging from about 0.01% to about 30% by weight, relative to the total weight of the cosmetic composition.

16. The cosmetic composition according to claim 1, further comprising at least one non-fluorescent direct dye chosen from nonionic, cationic and anionic direct dyes.

17. The cosmetic composition according to claim 16, wherein the at least one non-fluorescent direct dye is chosen from nitrobenzene dyes, azo dyes, anthraquinone dyes, naphthoquinone dyes, benzoquinone dyes, phenothiazine dyes, indigoid dyes, xanthene dyes, phenanthridine dyes, phthalocyanin dyes, and triaryl-methane-based dyes.

18. The cosmetic composition according to claim 16, wherein the at least one non-fluorescent direct dye is present in an amount ranging from about 0.0005% to about 12% by weight, relative to the total weight of the cosmetic composition.

19. The cosmetic composition according to claim 1, in the form of a lightening dyeing shampoo.

20. The cosmetic composition according to claim 1, further comprising at least one oxidation base chosen from para-phenylenediamines, bis(phenyl)alkylenediamines, para-aminophenols, ortho-aminophenols, heterocyclic bases, and acid and alkaline agent addition salts thereof.

21. The cosmetic composition according to claim 20, wherein the at least one oxidation base is present in an amount ranging from about 0.0005% to about 12% by weight, relative to the total weight of the cosmetic composition.

22. The cosmetic composition according to claim 20, further comprising at least one oxidizing agent.

23. The cosmetic composition according to claim 20, further comprising at least one coupler chosen from meta-phenylenediamines, meta-aminophenols, meta-diphenols, heterocyclic couplers, and acid and alkaline agent addition salts thereof.

24. The cosmetic composition according to claim 20, wherein the at least one coupler is present in an amount ranging from about 0.0001% to about 10% by weight, relative to the total weight of the cosmetic composition.

25. The cosmetic composition according to claim 23, further comprising at least one oxidizing agent.

26. The cosmetic composition according to claim 25, wherein the at least one oxidizing agent is chosen from hydrogen peroxide, urea peroxide, alkali metal bromates, persalts, and enzymes.

27. The cosmetic composition according to claim 26, wherein the persalts are chosen from perborates and persulphates.

28. The cosmetic composition according to claim 26, wherein the enzymes are chosen from peroxidases, two-electron, and four-electron oxidoreductases.

29. The cosmetic composition according to claim 26, wherein the at least one oxidizing agent comprises hydrogen peroxide.

30. A process for dyeing keratin materials with a lightening effect, comprising applying to the keratin materials a cosmetic composition comprising, in a cosmetically acceptable medium, at least one fluorescent dye that is soluble in the said medium, and at least one cationic polymer with a charge density of at least 1 meq/g;

wherein the at least one fluorescent dye is chosen from:

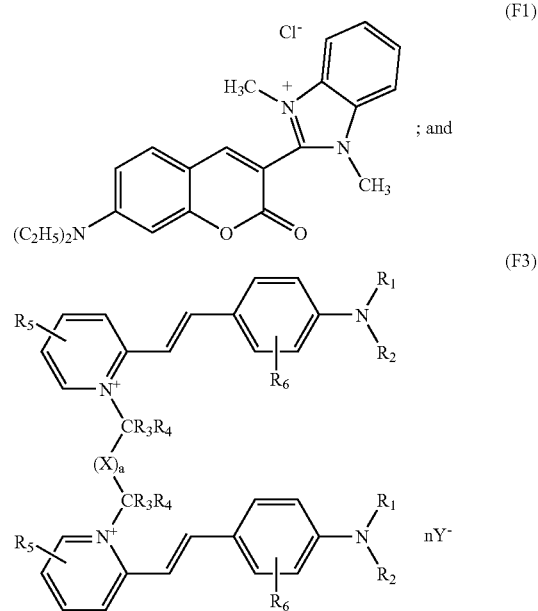

wherein:
$R_1$ and $R_2$, which may be identical or different, are chosen from:
  hydrogen atoms;
  linear and branched alkyl radicals comprising from 1 to 10 carbon atoms, optionally interrupted with at least one entity chosen from hetero atoms and groups comprising at least one hetero atom, and optionally substituted with at least one entity chosen from hetero atoms, groups comprising at least one hetero atom, and halogen atoms;
  aryl and arylalkyl radicals, wherein the aryl groups comprise 6 carbon atoms and the alkyl radicals comprise from 1 to 4 carbon atoms; the aryl radical is optionally substituted with at least one linear or branched alkyl radical comprising from 1 to 4 carbon atoms optionally interrupted with at least one entity chosen from hetero atoms and groups comprising at least one hetero atom and optionally substituted with at least one entity chosen from hetero atoms, groups comprising at least one hetero atom, and halogen atoms;
$R_1$ and $R_2$ may optionally be linked so as to form a heterocycle with the nitrogen atom and may further comprise at least one hetero atom, wherein the heterocycle may be optionally substituted with at least one linear or branched alkyl radical optionally interrupted with at least one entity chosen from hetero atoms and groups comprising at least one hetero atom, and/or optionally substituted with at least one entity chosen from hetero atoms, groups comprising at least one hetero atom, and halogen atoms;
$R_1$ or $R_2$ may also optionally be included in a heterocycle comprising the nitrogen atom and one of the carbon atoms of the phenyl group comprising the nitrogen atom;

R₃ and R₄, which may be identical or different, are chosen from hydrogen atoms and alkyl radicals comprising from 1 to 4 carbon atoms; R₅, which may be identical or different, is chosen from hydrogen atoms, halogen atoms, and linear and branched alkyl radicals comprising from 1 to 4 carbon atoms, optionally interrupted with at least one hetero atom;

R₆, which may be identical or different, is chosen from hydrogen atoms; halogen atoms; and linear and branched alkyl radicals comprising from 1 to 4 carbon atoms, optionally substituted with at least one entity chosen from hetero atoms, groups comprising at least one hetero atom, and halogen atoms, and/or interrupted with at least one entity chosen from hetero atoms and groups comprising at least one hetero atom;

X is chosen from:
linear and branched alkyl radicals comprising from 1 to 14 carbon atoms and alkenyl radicals comprising from 2 to 14 carbon atoms, optionally interrupted with at least one entity chosen from hetero atoms and groups substituted with at least one hetero atom, and/or optionally substituted with at least one entity chosen from hetero atoms, groups containing at least one hetero atom, and halogen atoms;

5- and 6-membered heterocyclic radicals optionally substituted with at least one entity chosen from linear and branched alkyl radicals comprising from 1 to 14 carbon atoms, optionally substituted with at least one hetero atom; linear and branched aminoalkyl radicals comprising from 1 to 4 carbon atoms, optionally substituted with at least one hetero atom; and halogen atoms;

fused and non-fused aromatic and diaromatic radicals, optionally separated with an alkyl radical comprising from 1 to 4 carbon atoms, wherein the aromatic and diaromatic radicals are optionally substituted with at least one entity chosen from halogen atoms and alkyl radicals comprising from 1 to 10 carbon atoms optionally substituted and/or interrupted with at least one hetero atom and/or group comprising at least one hetero atom;

dicarbonyl radicals;
the group X optionally comprising at least one cationic charge;
a is equal to 0 or 1;
Y⁻, which may be identical or different, is chosen from organic and mineral anions; and
n is an integer ranging from 2 to the number of cationic charges present in the fluorescent dye.

31. The process according to claim 30, wherein the at least one fluorescent dye provides a reflectance maximum that is in the wavelength range from about 500 to about 650 nanometers.

32. The process according to claim 31, wherein the at least one fluorescent dye provides a reflectance maximum that is in the wavelength range from about 550 to about 620 nanometers.

33. A process for dyeing human keratin fibers with a lightening effect, comprising:
a) a cosmetic composition comprising, in a cosmetically acceptable medium, at least one fluorescent dye that is soluble in the medium and at least one cationic polymer with a charge density of at least 1 meq/g;
with the proviso that the at least one fluorescent dye is not 2-[2-(4-dialkylamino)phenylethenyl]-1-alkylpyridinium wherein the alkyl radical of the pyridinium nucleus is chosen from methyl and ethyl radicals and wherein the radical of the benzene nucleus comprises a methyl radical, and wherein the counterion is a halide, and
wherein the at least one fluorescent dye is chosen from:

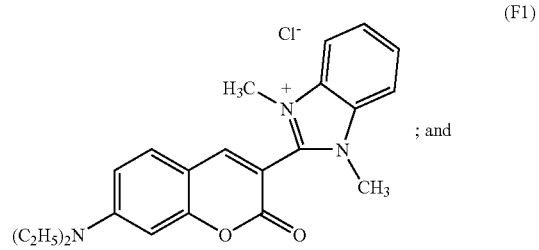

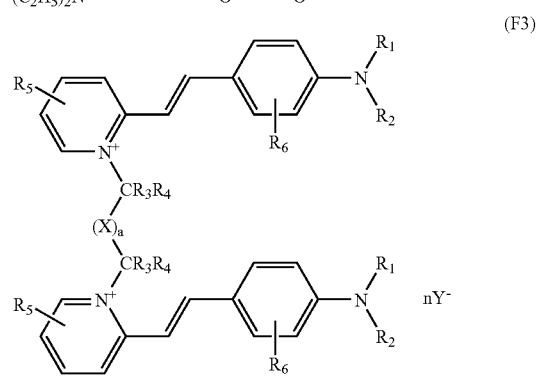

wherein:
R₁ and R₂, which may be identical or different, are chosen from:
hydrogen atoms;
linear and branched alkyl radicals comprising from 1 to 10 carbon atoms, optionally interrupted with at least one entity chosen from hetero atoms and groups comprising at least one hetero atom, and optionally substituted with at least one entity chosen from hetero atoms, groups comprising at least one hetero atom, and halogen atoms;
aryl and arylalkyl radicals, wherein the aryl groups comprise 6 carbon atoms and the alkyl radicals comprise from 1 to 4 carbon atoms; the aryl radical is optionally substituted with at least one linear or branched alkyl radical comprising from 1 to 4 carbon atoms optionally interrupted with at least one entity chosen from hetero atoms and groups comprising at least one hetero atom and optionally substituted with at least one entity chosen from hetero atoms, groups comprising at least one hetero atom, and halogen atoms;
R₁ and R₂ may optionally be linked so as to form a heterocycle with the nitrogen atom and may further comprise at least one hetero atom, wherein the heterocycle may be optionally substituted with at least one linear or branched alkyl radical optionally interrupted with at least one entity chosen from hetero atoms and groups comprising at least one hetero atom, and/or optionally substituted with at least one entity chosen from hetero atoms, groups comprising at least one hetero atom, and halogen atoms;

R₁ or R₂ may also optionally be included in a heterocycle comprising the nitrogen atom and one of the carbon atoms of the phenyl group comprising the nitrogen atom;

R₃ and R₄, which may be identical or different, are chosen from hydrogen atoms and alkyl radicals comprising from 1 to 4 carbon atoms;

R₅, which may be identical or different, is chosen from hydrogen atoms, halogen atoms, and linear and branched alkyl radicals comprising from 1 to 4 carbon atoms, optionally interrupted with at least one hetero atoms;

R₆, which may be identical or different, is chosen from hydrogen atoms; halogen atoms; and linear and branched alkyl radicals comprising from 1 to 4 carbon atoms, optionally substituted with at least one entity chosen from hetero atoms, groups comprising at least one hetero atom, and halooen atoms, and/or interrupted with at least one entity chosen from hetero atoms and groups comprising at least one hetero atom;

X is chosen from:
  linear and branched alkyl radicals comprising from 1 to 14 carbon atoms and alkenyl radicals comprising from 2 to 14 carbon atoms, optionally interrupted with at least one entity chosen from hetero atoms and groups substituted with at least one hetero atom, and/or optionally substituted with at least one entity chosen from hetero atoms, groups containing at least one hetero atom, and halogen atoms;
  5- and 6-membered heterocyclic radicals optionally substituted with at least one entity chosen from linear and branched alkyl radicals comprising from 1 to 14 carbon atoms, optionally substituted with at least one hetero atom; linear and branched aminoalkyl radicals comprising from 1 to 4 carbon atoms, optionally substituted with at least one hetero atom; and halogen atoms;
  fused and non-fused aromatic and diaromatic radicals, optionally separated with an alkyl radical comprising from 1 to 4 carbon atoms, wherein the aromatic and diaromatic radicals are optionally substituted with at least one entity chosen from halogen atoms and alkyl radicals comprising from 1 to 10 carbon atoms optionally substituted and/or interrupted with at least one hetero atom and/or group comprising at least one hetero atom;
  dicarbonyl radicals;
  the group X optionally comprising at least one cationic charge;

a is equal to 0 or 1;

Y³¹, which may be identical or different, is chosen from organic and mineral anions; and n is an integer ranging from 2 to the number of cationic charaes present in the fluorescent dye. is applied to the fibers, for a time that is sufficient to develop the desired coloration and lightening, b) the fibers are optionally rinsed,
c) the fibers are optionally washed with shampoo and rinsed, and
d) the fibers are dried or are left to dry.

34. The process according to claim 33, wherein the human keratin fibers have a tone height of less than or equal to 6.

35. The process according to claim 34, wherein human keratin fibers have a tone height of less than or equal to 4.

36. The process according to claim 33, wherein the human keratin fibers are artificially colored or pigmented.

37. The process according to claim 33, wherein the at least one fluorescent dye provides a reflectance maximum that is in the wavelength range of from about 500 to about 650 nanometers.

38. The process according to claim 37, wherein the at least one fluorescent dye provides a reflectance maximum that is in the wavelength range of from about 550 to about 620 nanometers.

39. A process for dyeing human keratin fibers with a lightening effect, comprising:
  a) a separately stored cosmetic composition comprising, in a cosmetically acceptable medium, at least one fluorescent dye that is soluble in the medium, at least one cationic polymer with a charge density of at least 1 meq/g, optionally comprising at least one oxidation base, at least one coupler and at least one non-fluorescent direct dye;
    with the proviso that the at least one fluorescent dye is not 2-[2-(4-dialkylamino)phenylethenyl]-1-alkylpyridinium wherein the alkyl radical of the pyridinium nucleus is chosen from methyl and ethyl radicals and wherein the radical of the benzene nucleus comprises a methyl radical, and wherein the counterion is a halide, and
  wherein the at least one fluorescent dye is chosen from:

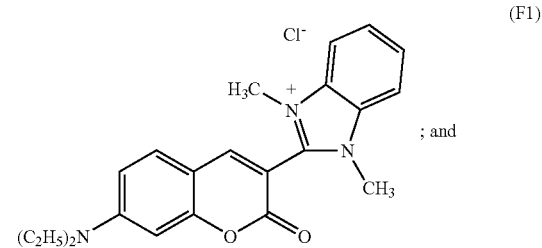

(F1)

; and

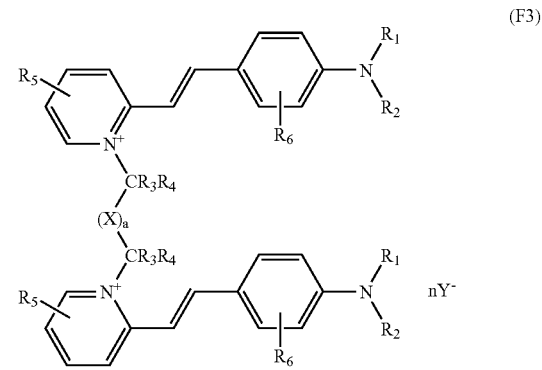

(F3)

wherein;
  R₁ and R₂, which may be identical or different, are chosen from:
    hydrogen atoms;
    linear and branched alkyl radicals comprising from 1 to 10 carbon atoms, optionally interrupted with at least one entity chosen from hetero atoms and groups comprising at least one hetero atom, and optionally substituted with at least one entity chosen from hetero atoms, groups comprising at least one hetero atom, and halogen atoms;
    aryl and arylalkyl radicals, wherein the aryl groups comprise 6 carbon atoms and the alkyl radicals comprise from 1 to 4 carbon atoms; the aryl radical is optionally substituted with at least one linear or branched alkyl radical comprising from 1 to 4 carbon atoms optionally interrupted with at least one entity chosen from hetero atoms and groups comprising at least one hetero atom and optionally substituted with at least one entity chosen from hetero atoms, groups comprising at least one hetero atom, and halogen atoms;

$R_1$ and $R_2$ may optionally be linked so as to form a heterocycle with the nitrogen atom and may further comprise at least one hetero atom, wherein the heterocycle may be optionally substituted with at least one linear or branched alkyl radical optionally interrupted with at least one entity chosen from hetero atoms and groups comprising at least one hetero atom, and/or optionally substituted with at least one entity chosen from hetero atoms, groups comprising at least one hetero atom, and halogen atoms;

$R_1$ or $R_2$ may also optionally be included in a heterocycle comprising the nitrogen atom and one of the carbon atoms of the phenyl group comprising the nitrogen atom;

$R_3$ and $R_4$, which may be identical or different, are chosen from hydrogen atoms and alkyl radicals comprising from 1 to 4 carbon atoms;

$R_5$, which may be identical or different, is chosen from hydrogen atoms, halogen atoms, and linear and branched alkyl radicals comprising from 1 to 4 carbon atoms, optionally interrupted with at least one hetero atoms;

$R_6$, which may be identical or different, is chosen from hydrogen atoms; halogen atoms; and linear and branched alkyl radicals comprising from 1 to 4 carbon atoms, optionally substituted with at least one entity chosen from hetero atoms, groups comprising at least one hetero atom, and halogen atoms, and/or interrupted with at least one entity chosen from hetero atoms and groups comprising at least one hetero atom;

X is chosen from:
linear and branched alkyl radicals comprising from 1 to 14 carbon atoms and alkenyl radicals comprising from 2 to 14 carbon atoms, optionally interrupted with at least one entity chosen from hetero atoms and groups substituted with at least one hetero atom, and/or optionally substituted with at least one entity chosen from hetero atoms, groups containing at least one hetero atom, and halogen atoms;

5- and 6-membered heterocyclic radicals optionally substituted with at least one entity chosen from linear and branched alkyl radicals comprising from 1 to 14 carbon atoms, optionally substituted with at least one hetero atom; linear and branched aminoalkyl radicals comprising from 1 to 4 carbon atoms, optionally substituted with at least one hetero atom; and halogen atoms;

fused and non-fused aromatic and diaromatic radicals, optionally separated with an alkyl radical comprising from 1 to 4 carbon atoms, wherein the aromatic and diaromatic radicals are optionally substituted with at least one entity chosen from halogen atoms and alkyl radicals comprising from 1 to 10 carbon atoms optionally substituted and/or interrupted with at least one hetero atom and/or group comprising at least one hetero atom;

dicarbonyl radicals;
the group X optionally comprising at least one cationic charge;

a is equal to 0 or 1;
$Y^{31}$, which may be identical or different, is chosen from organic and mineral anions; and n is an integer ranging from 2 to the number of cationic charges present in the fluorescent dye,
and another separately stored composition comprising in a cosmetically acceptable medium, at least one oxidizing agent, b) mixing the separately stored compositions together at the time of use, and applying to the fibers, for a time that is sufficient to develop the desired coloration and lightening, c) the fibers are optionally rinsed, d) the fibers are optionally washed with shampoo and rinsed, e) the fibers are dried or are left to dry.

40. The process according to claim 39, wherein the human keratin fibers have a tone height of less than or equal to 6.

41. The process according to claim 40, wherein human keratin fibers have a tone height of less than or equal to 4.

42. The process according to claim 39, wherein the human keratin fibers are artificially colored or pigmented.

43. A process for coloring dark skin with a lightening effect, comprising applying a cosmetic composition to the skin and wherein the skin is then dried or is left to dry, wherein said cosmetic composition comprises, in a cosmetically acceptable medium, at least one fluorescent dye that is soluble in the medium and at least one cationic polymer with a charge density of at least 1 meq/g;

with the proviso that the at least one fluorescent dye is not 2-[2-(4-dialkylamino)phenylethenyl]-1-alkylpyridinium wherein the alkyl radical of the pyridinium nucleus is chosen from methyl and ethyl radicals and wherein the radical of the benzene nucleus comprises a methyl radical, and wherein the counterion is a halide; and wherein the at least one fluorescent dye is chosen from:

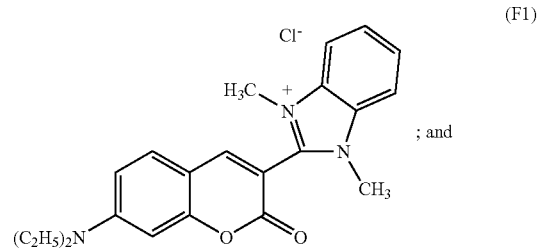

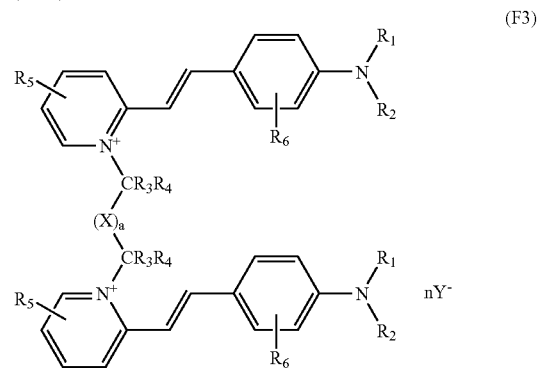

wherein:
$R_1$ and $R_2$, which may be identical or different, are chosen from:
hydrogen atoms;
linear and branched alkyl radicals comprising from 1 to 10 carbon atoms, optionally interrupted with at least one entity chosen from hetero atoms and groups comprising at least one hetero atom, and optionally substituted with at least one entity chosen from hetero atoms, groups comprising at least one hetero atom, and halogen atoms;

aryl and arylalkyl radicals, wherein the aryl groups comprise 6 carbon atoms and the alkyl radicals comprise from 1 to 4 carbon atoms; the aryl radical is optionally substituted with at least one linear or branched alkyl radical comprising from 1 to 4 carbon atoms optionally interrupted with at least one entity chosen from hetero atoms and groups comprising at least one hetero atom and optionally substituted with at least one entity chosen from hetero atoms, groups comprising at least one hetero atom, and halogen atoms;

$R_1$ and $R_2$ may optionally be linked so as to form a heterocycle with the nitrogen atom and may further comprise at least one hetero atom, wherein the heterocycle may be optionally substituted with at least one linear or branched alkyl radical optionally interrupted with at least one entity chosen from hetero atoms and groups comprising at least one hetero atom, and/or optionally substituted with at least one entity chosen from hetero atoms, groups comprising at least one hetero atom, and halogen atoms;

$R_1$ or $R_2$ may also optionally be included in a heterocycle comprising the nitrogen atom and one of the carbon atoms of the phenyl group comprising the nitrogen atom;

$R_3$ and $R_4$, which may be identical or different, are chosen from hydrogen atoms and alkyl radicals comprising from 1 to 4 carbon atoms;

$R_5$, which may be identical or different, is chosen from hydrogen atoms, halogen atoms, and linear and branched alkyl radicals comprising from 1 to 4 carbon atoms, optionally interrupted with at least one hetero atoms;

$R_6$, which may be identical or different, is chosen from hydrogen atoms; halogen atoms; and linear and branched alkyl radicals comprising from 1 to 4 carbon atoms, optionally substituted with at least one entity chosen from hetero atoms, groups comprising at least one hetero atom, and halogen atoms, and/or interrupted with at least one entity chosen from hetero atoms and groups comprising at least one hetero atom;

X is chosen from:
linear and branched alkyl radicals comprising from 1 to 14 carbon atoms and alkenyl radicals comprising from 2 to 14 carbon atoms, optionally interrupted with at least one entity chosen from hetero atoms and groups substituted with at least one hetero atom, and/or optionally substituted with at least one entity chosen from hetero atoms, groups containing at least one hetero atom, and halogen atoms;

5- and 6-membered heterocyclic radicals optionally substituted with at least one entity chosen from linear and branched alkyl radicals comprising from 1 to 14 carbon atoms optionally substituted with at least one hetero atom; linear and branched aminoalkyl radicals comprising from 1 to 4 carbon atoms optionally substituted with at least one hetero atom; and halogen atoms;

fused and non-fused aromatic and diaromatic radicals, optionally separated with an alkyl radical comprising from 1 to 4 carbon atoms, wherein the aromatic and diaromatic radicals are optionally substituted with at least one entity chosen from halogen atoms and alkyl radicals comprising from 1 to 10 carbon atoms optionally substituted and/or interrupted with at least one hetero atom and/or group comprising at least one hetero atom;

dicarbonyl radicals;

the group X optionally comprising at least one cationic charge;

a is equal to 0 or 1;

$Y^{31}$, which may be identical or different, is chosen from organic and mineral anions; and n is an integer ranging from 2 to the number of cationic charges present in the fluorescent dye.

44. A multi-compartment kit for dyeing and lightening keratin materials, comprising at least one compartment comprising a cosmetic composition comprising, in a cosmetically acceptable medium, at least one fluorescent dye that is soluble in the medium, at least one cationic polymer with a charge density of at least 1 meq/g, and optionally at least one oxidation base and optionally at least one coupler;

with the proviso that the at least one fluorescent dye is not 2-[2-(4-dialkylamino)phenylethenyl]-1-alkylpyridinium wherein the alkyl radical of the pyridinium nucleus is chosen from methyl and ethyl radicals and wherein the radical of the benzene nucleus comprises a methyl radical, and wherein the counterion is a halide; and wherein the at least one fluorescent dye is chosen from:

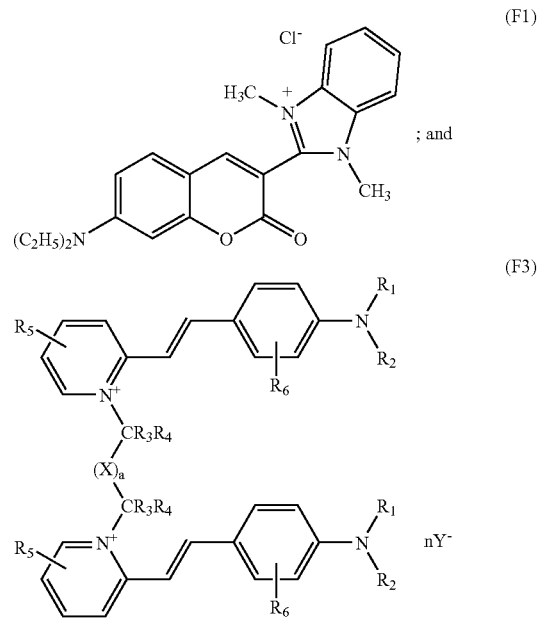

wherein:
$R_1$ and $R_2$, which may be identical or different, are chosen from:
hydrogen atoms;
linear and branched alkyl radicals comprising from 1 to 10 carbon atoms, optionally interrupted with at least one entity chosen from hetero atoms and groups comprising at least one hetero atom, and optionally substituted with at least one entity chosen from hetero atoms, groups comprising at least one hetero atom, and halogen atoms;

aryl and arylalkyl radicals, wherein the aryl groups comprise 6 carbon atoms and the alkyl radicals comprise from 1 to 4 carbon atoms; the aryl radical is optionally substituted with at least one linear or branched alkyl radical comprising from 1 to 4 carbon atoms optionally interrupted with at least one entity chosen from hetero atoms and groups comprising at least one hetero atom and optionally substituted with at least one entity chosen from hetero atoms, groups comprising at least one hetero atom, and halogen atoms;

$R_1$ and $R_2$ may optionally be linked so as to form a heterocycle with the nitrogen atom and may further comprise at least one hetero atom, wherein the heterocycle may be optionally substituted with at least one linear or branched alkyl radical optionally interrupted with at least one entity chosen from hetero atoms and groups comprising at least one hetero atom, and/or optionally substituted with at least one entity chosen from hetero atoms, groups comprising at least one hetero atom, and halogen atoms;

$R_1$ or $R_2$ may also optionally be included in a heterocycle comprising the nitrogen atom and one of the carbon atoms of the phenyl group comprising the nitrogen atom;

$R_3$ and $R_4$, which may be identical or different, are chosen from hydrogen atoms and alkyl radicals comprising from 1 to 4 carbon atoms;

$R_5$, which may be identical or different, is chosen from hydrogen atoms, halogen atoms, and linear and branched alkyl radicals comprising from 1 to 4 carbon atoms, optionally interrupted with at least one hetero atoms;

$R_6$, which may be identical or different, is chosen from hydrogen atoms; halogen atoms; and linear and branched alkyl radicals comprising from 1 to 4 carbon atoms, optionally substituted with at least one entity chosen from hetero atoms, groups comprising at least one hetero atom, and halogen atoms, and/or interrupted with at least one entity chosen from hetero atoms and groups comprising at least one hetero atom;

X is chosen from:
linear and branched alkyl radicals comprising from 1 to 14 carbon atoms and alkenyl radicals comprising from 2 to 14 carbon atoms, optionally interrupted with at least one entity chosen from hetero atoms and groups substituted with at least one hetero atom, and/or optionally substituted with at least one entity chosen from hetero atoms, groups containing at least one hetero atom, and halogen atoms;

5- and 6-membered heterocyclic radicals optionally substituted with at least one entity chosen from linear and branched alkyl radicals comprising from 1 to 14 carbon atoms, optionally substituted with at least one hetero atom; linear and branched aminoalkyl radicals comprising from 1 to 4 carbon atoms, optionally substituted with at least one hetero atom; and halogen atoms;

fused and non-fused aromatic and diaromatic radicals, optionally separated with an alkyl radical comprising from 1 to 4 carbon atoms, wherein the aromatic and diaromatic radicals are optionally substituted with at least one entity chosen from halogen atoms and alkyl radicals comprising from 1 to 10 carbon atoms optionally substituted and/or interrupted with at least one hetero atom and/or group comprising at least one hetero atom;

dicarbonyl radicals;

the group X optionally comprising at least one cationic charge;

a is equal to 0 or 1;

$Y^{31}$, which may be identical or different, is chosen from organic and mineral anions; and n is an integer ranging from 2 to the number of cationic charaes present in the fluorescent dye;

and at least one other compartment comprising a composition comprising at least one oxidizing agent.

45. The multi-compartment kit according to claim 44, wherein the keratin materials are chosen from artificially colored and natural keratin fibers.

* * * * *

UNITED STATES PATENT AND TRADEMARK OFFICE
CERTIFICATE OF CORRECTION

PATENT NO.         : 7,195,651 B2
APPLICATION NO.    : 10/814335
DATED              : March 27, 2007
INVENTOR(S)        : Grégory Plos et al.

It is certified that error appears in the above-identified patent and that said Letters Patent is hereby corrected as shown below:

In claim 1, column 30, line 18, "wherein;" should read --wherein:--.

In claim 1, column 30, line 63, "atoms;" should read --atom;--.

In claim 17, column 35, line 20, "triaryl-methane-based" should read --triarylmethane-based--.

In claim 33, column 39, line 12, "atoms;" should read --atom;--.

In claim 33, column 39, line 18, "halooen" should read --halogen--.

In claim 33, column 39, line 51, "$Y^{31}$," should read --$Y^-$,--.

In claim 33, column 39, line 54, "charaes" should read --charges--.

In claim 33, column 39, line 54, "dye." should read --dye,--.

In claim 39, column 40, line 52, "wherein;" should read --wherein:--.

In claim 39, column 41, line 29, "atoms;" should read --atom;--.

In claim 39, column 41, line 66, "$Y^{31}$," should read --$Y^-$,--.

In claim 43, column 43, line 37, "atoms;" should read --atom;--.

In claim 43, column 44, line 10, "$Y^{31}$," should read --$Y^-$,--.

In claim 44, column 45, line 34, "atoms;" should read --atom;--.

In claim 44, column 46, line 32, "$Y^{31}$," should read --$Y^-$,--.

UNITED STATES PATENT AND TRADEMARK OFFICE
CERTIFICATE OF CORRECTION

PATENT NO. : 7,195,651 B2
APPLICATION NO. : 10/814335
DATED : March 27, 2007
INVENTOR(S) : Grégory Plos et al.

It is certified that error appears in the above-identified patent and that said Letters Patent is hereby corrected as shown below:

In claim 44, column 46, line 35, "charaes" should read --charges--.

Signed and Sealed this

Twenty-second Day of May, 2007

JON W. DUDAS
*Director of the United States Patent and Trademark Office*